(12) United States Patent
Lozano-Dubernard et al.

(10) Patent No.: US 10,758,608 B2
(45) Date of Patent: Sep. 1, 2020

(54) VACCINE IN THE FORM OF A RECOMBINANT SERO TYPE 9 AVIAN ADENOVIRUS VECTOR

(71) Applicant: GRUPO INDUSTRIAL PECUARIO, S.A. DE C.V., Mexico City (MX)

(72) Inventors: Bernardo Lozano-Dubernard, Del. Coyoacán (MX); Ernesto Soto-Priante, Col. Jardines del Pedregal (MX); David Sarfati-Mizrahi, Huixquilucan (MX)

(73) Assignee: GRUPO INDUSTRIAL PECUARIO, S.A. DE C.V., Mexico City (MX)

( * ) Notice: Subject to any disclaimer, the term of this patent is extended or adjusted under 35 U.S.C. 154(b) by 0 days.

(21) Appl. No.: 15/502,443

(22) PCT Filed: Aug. 6, 2015

(86) PCT No.: PCT/IB2015/055994
§ 371 (c)(1),
(2) Date: Feb. 7, 2017

(87) PCT Pub. No.: WO2016/020885
PCT Pub. Date: Feb. 11, 2016

(65) Prior Publication Data
US 2017/0232096 A1    Aug. 17, 2017

(30) Foreign Application Priority Data

Aug. 8, 2014 (WO) .................. PCT/IB2014/063809

(51) Int. Cl.
| | |
|---|---|
| *A61K 39/145* | (2006.01) |
| *A61K 39/245* | (2006.01) |
| *C07K 14/005* | (2006.01) |
| *C12N 15/86* | (2006.01) |
| *C12N 7/00* | (2006.01) |
| *A61K 39/12* | (2006.01) |
| *A61K 39/00* | (2006.01) |

(52) U.S. Cl.
CPC ............ *A61K 39/145* (2013.01); *A61K 39/12* (2013.01); *A61K 39/245* (2013.01); *C07K 14/005* (2013.01); *C12N 7/00* (2013.01); *C12N 15/86* (2013.01); *A61K 2039/5252* (2013.01); *A61K 2039/5256* (2013.01); *A61K 2039/545* (2013.01); *A61K 2039/70* (2013.01); *C12N 2710/10221* (2013.01); *C12N 2710/10234* (2013.01); *C12N 2710/10243* (2013.01); *C12N 2710/10271* (2013.01); *C12N 2710/16034* (2013.01); *C12N 2710/16071* (2013.01); *C12N 2760/16134* (2013.01); *C12N 2760/16171* (2013.01)

(58) Field of Classification Search
None
See application file for complete search history.

(56) References Cited

U.S. PATENT DOCUMENTS

| | | | | |
|---|---|---|---|---|
| 5,804,195 | A | * | 9/1998 | Gutter .................... A61K 39/12 424/202.1 |
| 6,296,852 | B1 | | 10/2001 | Johnson et al. |
| 6,406,702 | B1 | * | 6/2002 | Sharma .................. A61K 39/12 424/199.1 |
| 2010/0003279 | A1 | * | 1/2010 | Hideyuki ............... A61K 39/12 424/207.1 |
| 2011/0268762 | A1 | * | 11/2011 | Toro ....................... A61K 39/12 424/205.1 |
| 2017/0232096 | A1 | * | 8/2017 | Lozano-Dubernard ..................... A61K 39/145 424/199.1 |

FOREIGN PATENT DOCUMENTS

| | | |
|---|---|---|
| WO | WO 94/24268 | 10/1994 |
| WO | WO 2010/058236 A1 | 5/2010 |

OTHER PUBLICATIONS

WIPO English translation of Lozano-Dubernard et al. (WO 2010/058236) May 2010.*
Marek et al. (Veterinary Microbiology. 2013; 166: 250-256).*
Schachner et al. Fowl adenovirus-induced diseases and strategies for their control—a review on the current global situation. 1 Avian Pathology (2017): 1-16.*
Sequence alignment of SEQ ID No. 1 with GenEmbl database access No. EU979376.1 by Steer et al 2009 in Journal of Clinical Microbiology.*
J.C. Corredor et al., "The Non-Essential Left End Region of the Fowl Adenovirus 9 Genome is Suitable for Foreign Gene Insertion/Replacement," Virus Research 149, 2010, pp. 167-174.
J.C. Corredor et al., "Antibody Response and Virus Shedding of Chickens Inoculated with Left End Deleted Fowl Adenovirus 9-Based Recombinant Viruses," Avian Diseases, 2011 55(3), pp. 443-446, URL: http://www.bioone.org/doi/full/10.1637/9710-031311-Reg.1.
(Continued)

*Primary Examiner* — Shanon A. Foley
(74) *Attorney, Agent, or Firm* — Finnegan, Henderson, Farabow, Garrett & Dunner LLP

(57) ABSTRACT

A recombinant vaccine comprising a serotype 9 fowl adenovirus vector (FAdV-9) having at least one exogenous nucleotide sequence inserted encoding at least one antigen of a disease of interest and replacing the adenovirus genome non-essential region, and a pharmaceutically acceptable vehicle, adjuvant and/or excipient, wherein the at least one exogenous nucleotide sequence encoding at least one antigen of a disease of interest and replacing the adenovirus genome non-essential region is located between the 491 and 2782 nucleotides. The vector of this vaccine is stable for industrial scale production. When administering this vaccine in combination with a vaccine against Marek's disease, both vaccines produce an adequate immune response which is not affected by interference between each other. In the same way, effectiveness of the recombinant vaccine is not affected by maternal antibodies, and is capable of inducing both an early and lasting protective response, even with only one application.

20 Claims, 19 Drawing Sheets

Specification includes a Sequence Listing.

(56) References Cited

OTHER PUBLICATIONS

L. Deng et al., "Oral Inoculation of Chickens with a Candidate Fowl Adenovirus 9 Vector," Clinical and Vaccine Immunology, Aug. 2013, vol. 20, No. 8, pp. 1189-1196.

M.A. Johnson et al., "A Recombinant Fowl Adenovirus Expressing the S1 Gene of Infectious Bronchitis Virus Protects Against Challenge with Infectious Bronchitis Virus," Vaccine, Mar. 13, 2003, vol. 21 (21-22), pp. 2730-2736.

International Search Report for International Application No. PCT/IB2015/055994, dated Dec. 12, 2015.

M. Sheppard et al., "Fowl Adenovirus Recombinant Expressing VP2 of Infectious Bursal Disease Virus Induces Protective Immunity Against Bursal Disease," Archives of Virology, 1998, vol. 143 (5), pp. 915-930.

D.H. Yang, "Development of Fowl Adenovirus 9 Based Vector Vaccine Expressing the Hemagglutinin Gene of an H5N1 Influenza Virus," 20 Years of ESVV: Integrating Classical and Molecular Virology, Programme & Proceedings, 8$^{th}$ International Congress of Veterinary Virology, Aug. 23-26, 2009, Budapest, Hungary.

Elliot, A., "Comparing influenza virus hemagglutinin (HA) expression in three different baculovirus expression systems," Thesis presented to the University of Geulph, ON, Canada, copyright Aug. 2012, 144 pages.

Niczyporuk et al., "Effect of fowl adenovirus on replication of vaccine strain of Marek's disease virus in chickens," Bull Vet Inst Pulawy 57, 467-472, 2013.

Spackman et al., "Variation in protection of four divergent avian influenza virus vaccine seed strains against eight clade 2.2.1 and 2.2.1.1. Egyptian H5N1 high pathogenicity variants in poultry," Influenza Other Respir Viruses, 2014, 8(6):654-662.

Cha et al., "Suboptimal protection against H5N1 highly pathogenic avian influenza viruses from Vietnam in ducks vaccinated with commercial poultry vaccines," Vaccine, 2013, 31(43):4953-4960.

Sylte et al., "Influenza neuraminidase antibodies provide partial protection for chickens against high pathogenic avian influenza infection," Vaccine, 2007. 25(19):3763-3772.

\* cited by examiner

VACCINE IN THE FORM OF A RECOMBINANT SERO TYPE 9 AVIAN ADENOVIRUS VECTOR

CROSS REFERENCE TO RELATED APPLICATIONS

This application is a national stage entry under 35 U.S.C. § 371 of International Application No. PCT/IB2015/055994 filed on Aug. 6, 2015, and claims priority to and the benefit of the filing date of International Application No. PCT/IB2014/063809 filed on Aug. 8, 2014, the entire contents of which are incorporated by reference herein.

FIELD OF THE INVENTION

The present invention is related to vaccines based on viral vectors, and more particularly it is related to a vaccine based on a serotype-8 fowl adenovirus recombinant vector.

BACKGROUND OF THE INVENTION

Adenoviruses are linear, double-stranded, DNA viruses, from 70-90 nm diameter, nonenveloped, and having an icosahedral-shaped capside, which is formed by 240 hexons, 12 pentons and fibers extending from each icosahedral apex. These hexons, pentons and fibers represent the major adenovirus antigens, and those that determine the serotype thereof.

The adenoviruses genome is about 30-45 kb in size, and has four early regions (E1, E2, E3 and E4), and five late regions (L1-L5).

Adenoviruses have been isolated from different species, the two main genres being Aviadenovirus, isolated from birds, and Mastadenovirus, isolated from mammals.

Adenoviruses are considered good candidates as recombinant vectors for vaccine production because they are highly infectious and many of them are not pathogenic. In addition, adenovirus vectors can efficiently translate large-size genes, and generate an extended immune response in animals. Nonetheless, it is also known that the adenoviruses specific structure requires the study of the specific insertion sites of heterologous genes for each species, and that it is virtually impossible to generalize on the biological behavior of the various known adenoviruses when being converted into a recombinant viral vector.

So far, human, simian, avian, porcine, among others, adenoviruses have been utilized as vectors for potential use as recombinant vaccines. In particular, it is known that fowl adenoviruses (FadV) are potential candidates for the elaboration of recombinant vaccines. Nonetheless, as will be described below, the possibility of successfully utilizing them at a commercial level, particularly in the veterinary industry, has been generally inhibited due to the inability to reach their large-scale production with the required stability, since the production of adenoviruses is carried out from cell lines which yields are typically very poor, or which nature prevents achieving a stability of the viral vector in successive passes, whereby it is easy to understand that nowadays there are no vectorized vaccines in avian adenoviruses.

For example, International Publication No. WO94/24268 describes FAdV recombinant vectors having at least one heterologous nucleotide sequence inserted, and which are useful in generating an immune response in birds susceptible to diseases. According to this document, the non-essential regions of the adenoviral genome that may be appropriate for the heterologous gene to be replaced or inserted in, are those located at the genome right terminal end, preferably the region located between 0.0038 and 0.0039 in (97 and 99.9 m.u.) The recombinant vaccine, according to that document, could apparently be utilized in combination with vaccines against other viruses, such as that of Marek's disease or Newcastle's disease, without having evidence of this. Additionally, in this document the behavior of the adenovirus obtained after successive passes in cell lines for large-scale production is not illustrated either.

Also, U.S. Pat. No. 6,296,852 describes serotype-9 FAdV vectors (FAdV-9) wherein an insertion of nucleotide heterologous sequences into non-essential regions of the viral genome is carried out. These regions can be non-encoding regions located in the genome left and/or right end, preferably at the region located on the right end (3'), between 0.0023 and 0.0039 in (60 and 100 m.u.) As for the WO94/24268 document, although this patent identifies another wider region for the potential insertion of exogenous genes, it does not illustrate its behavior, and particularly, its integrity either, after successive passes in cell lines.

In another document (Corredor, J. C. and Nagy, E., the non-essential left end region of the fowl adenovirus 9 genome is suitable for foreign gene insertion/replacement. Virus Research. Vol 149, 167-174; 2010), it is disclosed that the 5' end non-essential region of the FAdV-9 genome, could also be a suitable site for the insertion or replacement by exogenous genes to produce recombinant vectors. For example, one of such vectors was obtained replacing the non-essential region located between the 491-2782 nucleotides with the gene encoding for an enhanced green fluorescent protein (EGFP). This document, however, like the others, does not show whether or not the viral vectors as built would be stable when inserting an exogenous gene encoding for the antigen of a disease into them, and by replicating them in suitable cell systems to obtain a recombinant vaccine, since the document only shows a reporter gene expression and lacks in vivo assays; besides it does not mention the composition or the protection levels against a disease of interest either.

As may be seen, it is known that the non-essential regions of the FAdV genome represent potential sites where an exogenous nucleotide sequence may be inserted or replaced. However, the vectors described in the state of the art have the disadvantage of being non-stable at the time of producing recombinant vaccines at an industrial level, due to the loss of the heterologous gene inserted after various passes in cell cultures.

Further, in the state of the art, the use of adenoviral vectors in the treatment of birds, mainly poultry, has been avoided due to its interference with vaccines against Marek's disease, vaccines that are widely utilized in the avian industry. Marek's disease (EM) is a condition caused by a herpesvirus affecting domestic birds, causing a lymphoproliferative disease provoking legs or wings paralysis, and lymphoid tumors, as well as mortality. In order to prevent this disease, monovalent or polyvalent active vaccines are applied, mainly subcutaneously or in-ovo.

In order to reduce costs and achieve greater efficiency at the time of application, sometimes the co-administration of at least two vaccines is preferred. However, although documents like the above-mentioned International Publication No. WO94/24268 expose the possibility of utilizing adenoviruses in combination with Marek's vaccines; subsequent studies have demonstrated that adenovirus vaccines and Marek's virus vaccines have severe in-field interferences when mortality rate and lesions produced by both diseases on birds, preferably long-living, are analyzed, like commercial stance hens.

Currently it is now known that by simultaneously applying a whole virus vaccine against EM with a recombinant vaccine in an adenovirus vector, the vaccine against EM might interfere with the recombinant vaccine due to the following mechanisms: a) different replication kinetics; b) the vaccines compete for the same cell-type for their replication in birds; and c) the EM virus causes immunosuppression in birds. Apparently, if this interference is to be overcome, and to achieve an effective vaccination against the disease related to the exogenous gene of the recombinant vaccine, it would be necessary to administer a higher dose of said recombinant vaccine, or reduce the dose of the vaccine against EM (Breedlove et al., Avian influenza adenovirus-vectored in-ovo vaccination; target embryo tissues and combination with Marek's disease vaccine. Avian Disease. Vol. 55, 667-673; 2011). However, the same Breedlove's et al. reference shows that increasing the doses of the adenovirus recombinant vaccine could cause a temporary interference with the vaccine against EM which makes it ineffective, causing severe problems in the field. This means that, up to date, a vaccine based on a recombinant adenovirus viral vector has not been able to be formulated with an exogenous gene which does not interfere with the protection conferred by the Marek's disease vaccine or vice versa.

Likewise, maternal antibodies are another factor which can potentially cause interference with a vaccine. Although maternal antibodies confer protection to newborn animals, their presence may inhibit or reduce the vaccines effects, causing the immune-response produced thereby to be non-optimal.

Another challenge found in the development of vaccines in general is the time in which protection and duration of said protection is achieved, as a function of the formula utilized for the vaccine.

A vaccines which grants early protection, that is to say, in a very short time starting from the application, will also have a short-term effect since the levels of protection will drop rapidly, making a periodic re-vaccination necessary. In contrast, a vaccine which grants durable or long-lasting protection will take more time to achieve protection (late protection), although said protection will last for a longer time, normally requiring less re-vaccination in order to achieve the protective effect desired. Normally, to achieve lasting protection in a group of animals it is necessary to apply early protection vaccines in combination with late protection vaccines in order to avoid the possibility that the animals get sick along their entire development.

In the state of the art it is known that an active virus vaccine normally grants quick or early protection, since it achieves an acceptable, but not lasting, level of protection in a short-time range starting from its application. On the other hand, it is also known that deactivated viruses vaccines grant a more lasting protection than that of the active virus, but do not require long times to achieve it, that is to say, the protection is late and in many cases they also require re-vaccination, although less frequent.

For example, Stine et al. (Evaluation of inactivated newcastle disease, avian diseases, Vol. 24, No. 1 (January-March, 1980), pp. 99-111) assessed three vaccines against NDV: a deactivated vaccine in emulsion, a deactivated vaccine adsorbed in $Al(OH)_3$ and an alive commercial vaccine, finding that the alive vaccine produces HI titers in chickens a week before the deactivated vaccines do, whereas the deactivated vaccine in emulsion produces a sustained immune response.

Likewise, Folitse et al. (Efficacy of combined killed-in-oil emulsion and alive newcastle disease vaccines in chickens, Avian Diseases, Vol. 42, No. 1 (January-March, 1998), pp. 173-178) mention that there are reports that the NDV deactivated vaccines, emulsified in oil, induce high and lasting levels of circulating antibodies in birds that were previously vaccinated with active vaccines. Likewise, they mention that the reason why a high antibody response is obtained upon administration of an NDV deactivated vaccine, in combination with an active vaccine against the same disease, could be due to the fact that at the beginning the alive virus replicates rapidly, eliciting a primary immune response, which is followed by a continuous but slow release of the antigen of a deactivated vaccine, which behaves like a reinforcing dose.

Also, Toro et. al (Avian influenza mucosal vaccination in chickens with replication-defective recombinant adenovirus vaccine, Avian Diseases 55:43-47, 2011) assessed the protection conferred by a recombinant adenovirus vaccine free of adenovirus competent for the replication that would express the avian influenza H5 gene optimized in its codons, which was applied on 5 days old laying type birds, and in some cases with re-vaccination when they turned 15 days old. The results showed that only the birds which were re-vaccinated developed high antibody titers. These titers could be detected starting from the age of 9 days, reaching their maximum at the age of 32 days.

In like manner, there are some active viruses that extraordinarily provide both early and lasting protection, just like the Marek virus. Nonetheless, the Marek virus can be utilized as a vector and in the state of the art it has demonstrated to achieve early and lasting protection against Marek's disease with only one application, but for the inserted exogenous antigen, it does not achieve early protection, but it only presents late and lasting protection.

As can be seen from the state of the art, it has not been possible to successfully utilize adenoviruses and, in particular, serotype 9 avian adenovirus FAdV-9 in the state of the art as a recombinant vaccine for birds with any exogenous gene at an industrial scale, although diverse insertion sites have been described, on the one hand due to the fact that adequate stability is not achieved in their reproduction on cell lines after successive passes, and on the other hand due to the fact that the Marek's disease vaccine interferes with the action mechanism of adenoviruses or vice versa, reason for which the use of adenoviruses in combination with Marek's disease vaccines has been expressly avoided in the state of the art. Further, it has not been possible to obtain a viral recombinant vaccine which achieves both early and lasting protection for an exogenous antigen inserted in the viral vector utilized with only one application.

SUMMARY

Considering the drawbacks of the prior art, it is an object of the present invention to provide a recombinant vaccine in a serotype-9 fowl adenovirus, wherein said vector is stable when manufactured at an industrial level.

It is another object of the present invention to provide a recombinant vaccine which, even if it is administered in combination with a vaccine against Marek's disease, both vaccines produce an adequate immune response which is not affected by interference between each other.

An additional object of the present invention is to provide a recombinant vaccine which effectiveness is not affected by maternal antibodies, and which induces an optimal immune-response.

It is still another object of the present invention to count on a recombinant vaccine which induces both a protective, that is to say, within the first 19 days starting from its application, and lasting, that is to say, up to at least 90 days after its application, protective response.

It is still another object of the present invention to count on a recombinant vaccine which achieves, with only one application, both early and lasting protection for a disease related to the exogenous antigen inserted in a viral vector contained in said vaccine.

BRIEF DESCRIPTION OF THE DRAWINGS

Novel aspects considered characteristic of the present invention will be established particularity in the appended claims. However, some embodiments, characteristics and some objects and advantages thereof will be better understood from the detailed description, when read related to the appended drawings, wherein:

DETAILED DESCRIPTION OF THE INVENTION

Figure 1A:
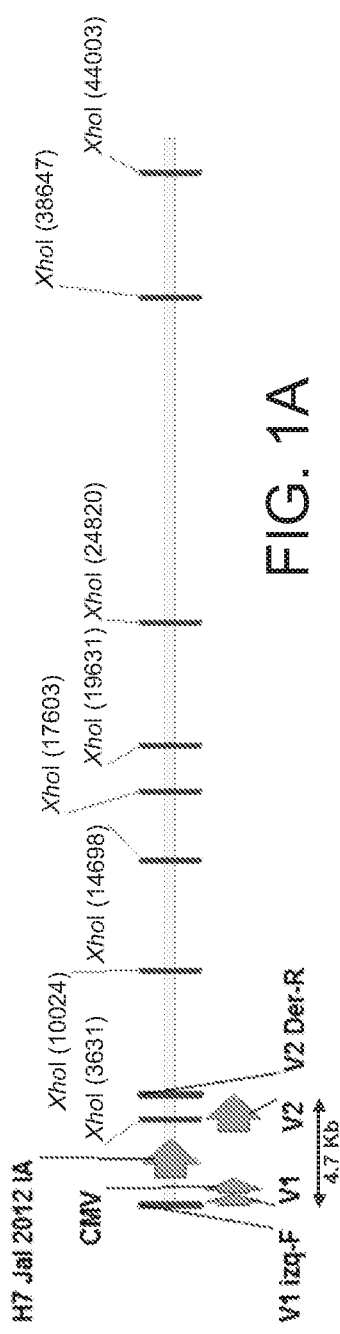
FIG. 1A is the DNA restriction map of an FAdV-9 recombinant virus with an avian influenza HA insert, built according to the present invention.
Figure 1B:
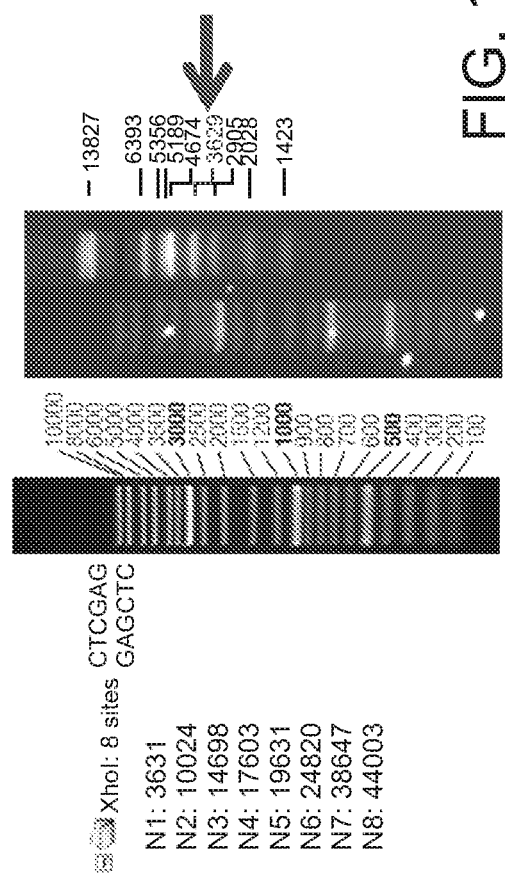
FIG. 1B is an agarose gel in which DNA fragments of the FAdV-9 recombinant virus with an avian influenza HA insert are shown, built according to the present invention, obtained by restriction enzyme digestion.
Figure 1C:
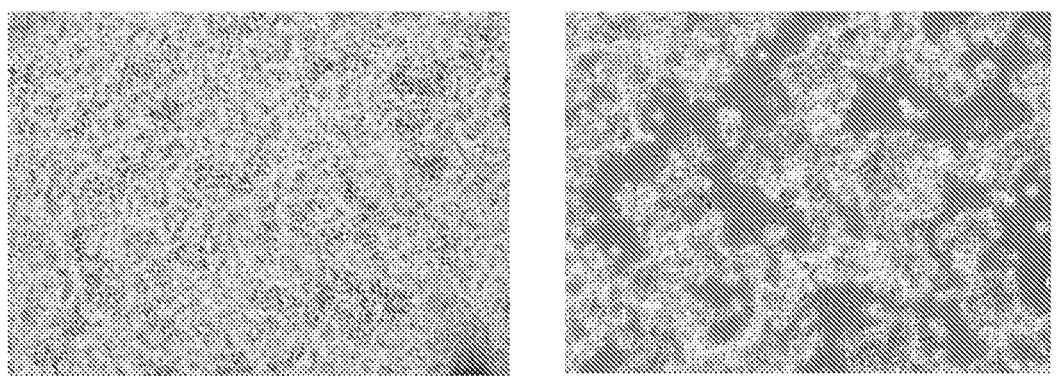
FIG. 1C is a non-infected CeLi cell culture, and one infected with an FAdV-9 recombinant virus with an avian influenza HA insert, built according to the present invention.
Figure 2A:
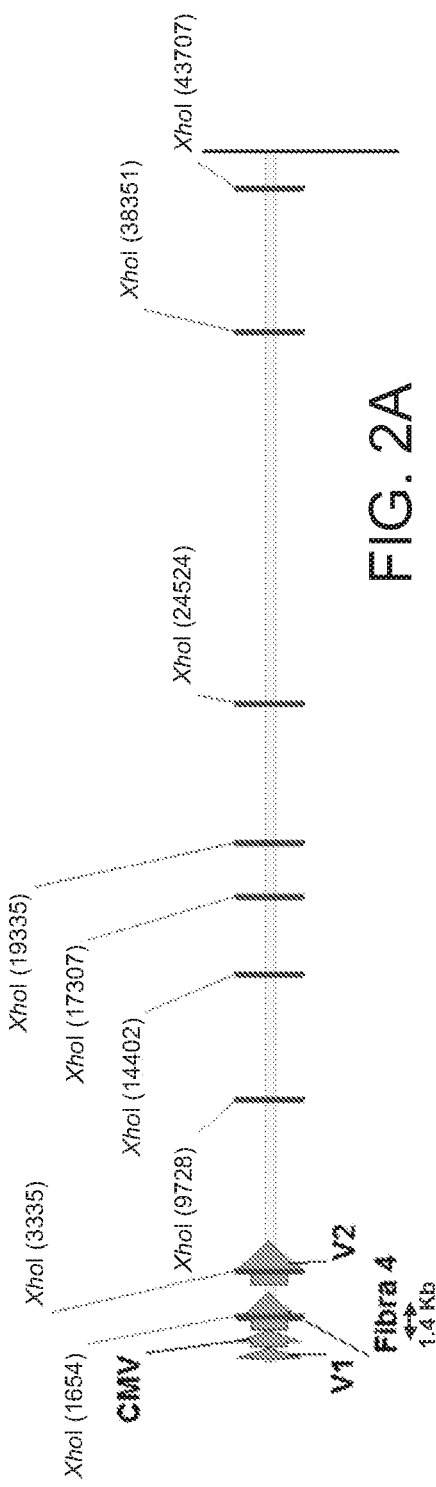
FIG. 2A shows the DNA restriction map of an FAdV-9 recombinant virus with a hepatitis Fiber-4 insert having inclusion bodies, built according to the present invention.
Figure 2B:
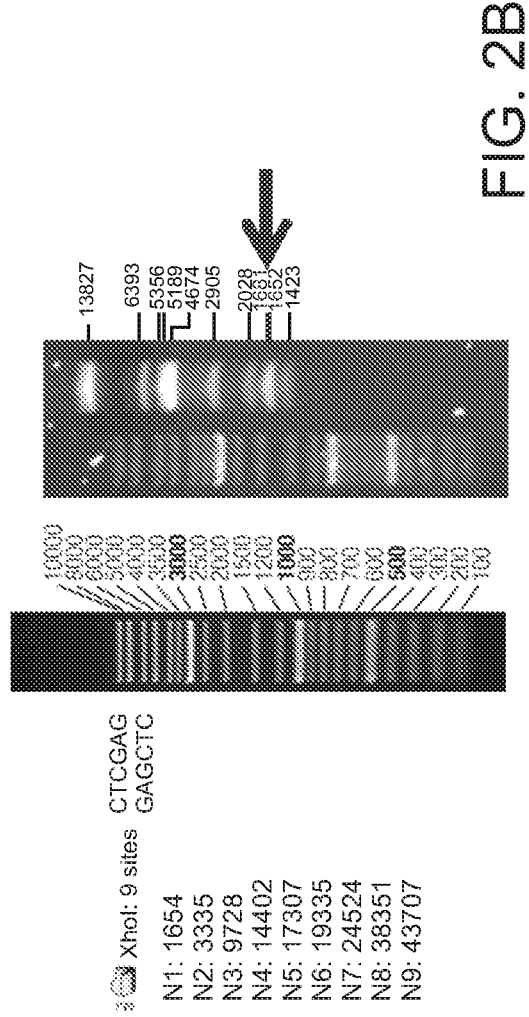
FIG. 2B is an agarose gel wherein ADN fragments of the FAdV-9 recombinant virus with a hepatitis Fiber-4 insert having inclusion bodies are shown, built according to the present invention, obtained by restriction enzyme digestion.
Figure 2C:
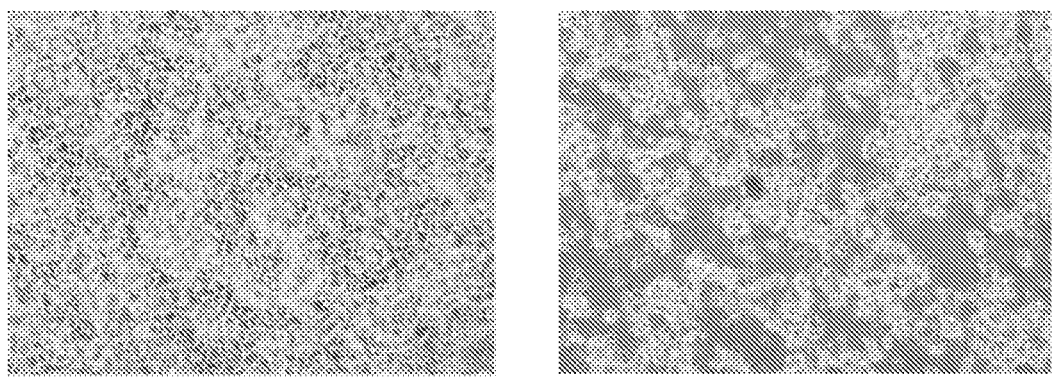
FIG. 2C is a non-infected CeLi cell culture, and one infected with a FAdV-9 recombinant virus with a hepatitis Fiber-4 insert having inclusion bodies, built according to the present invention.
Figure 3A:
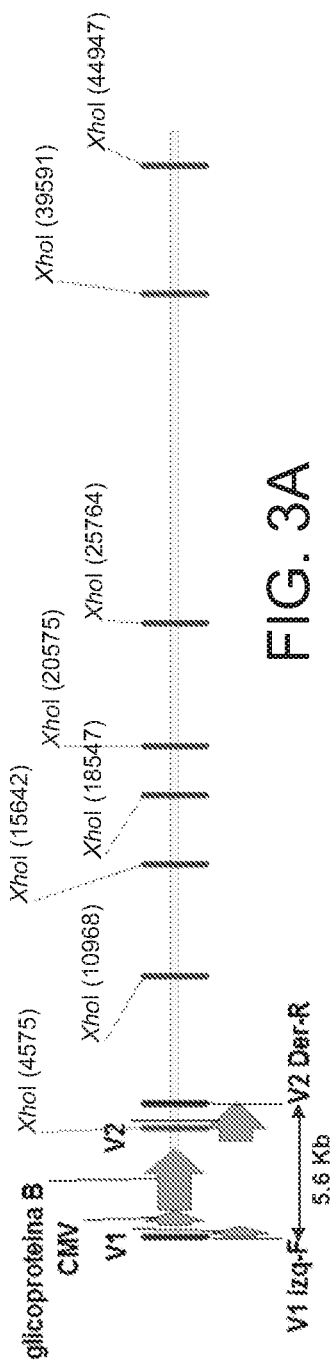
FIG. 3A shows the DNA restriction map of the FAdV-9 recombinant virus with a glycoprotein-B insert of the infectious laryngotracheitis virus in birds, built according to the present invention.
Figure 3B:
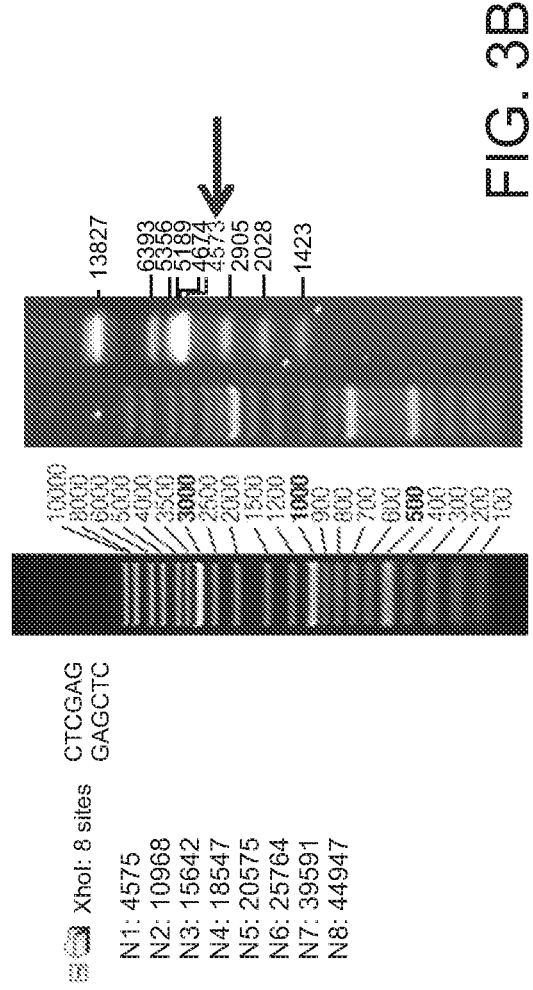
FIG. 3B is an agarose gel wherein DNA fragments of the FAdV-recombinant virus with a glycoprotein-B insert of the infectious laryngotracheitis virus in birds are shown, built according to the present invention, obtained by restriction enzyme digestion.
Figure 3C:
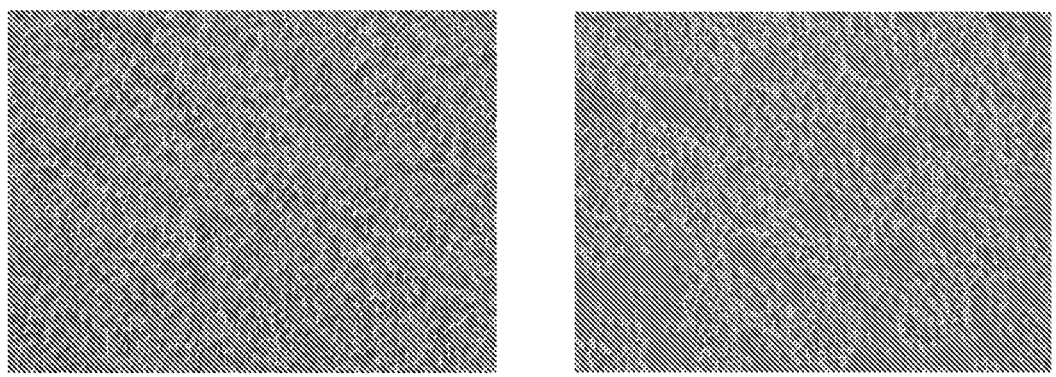
FIG. 3C is a non-infected CeLi cell culture, and one infected with a FAdV-9 recombinant virus with a glycoprotein-B insert of the infectious laryngotracheitis virus in birds, built according to the present invention.
Figure 4A:
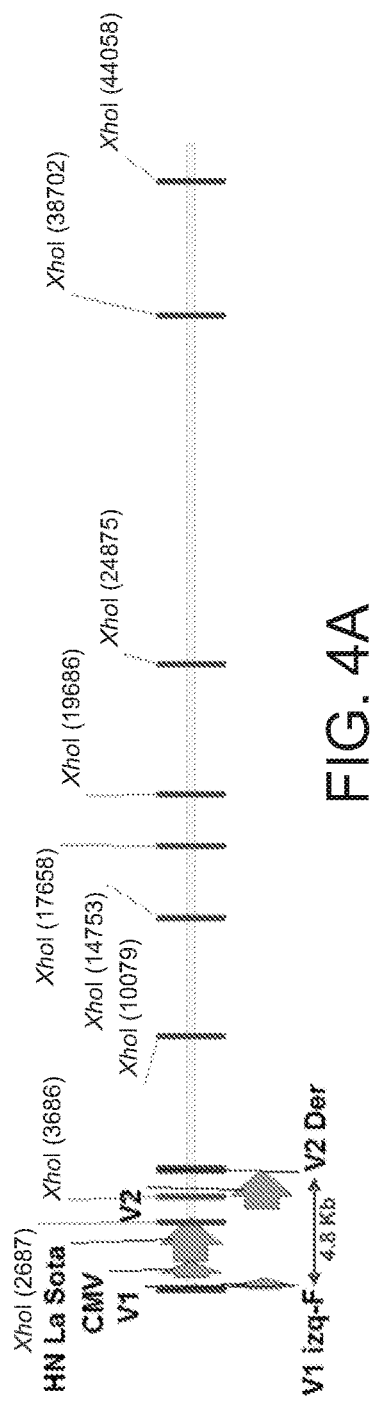
FIG. 4A is the DNA restriction map of the FAdV-9 recombinant virus with a HN protein insert of the Newcastle's disease virus, built according to the present invention.
Figure 4B:
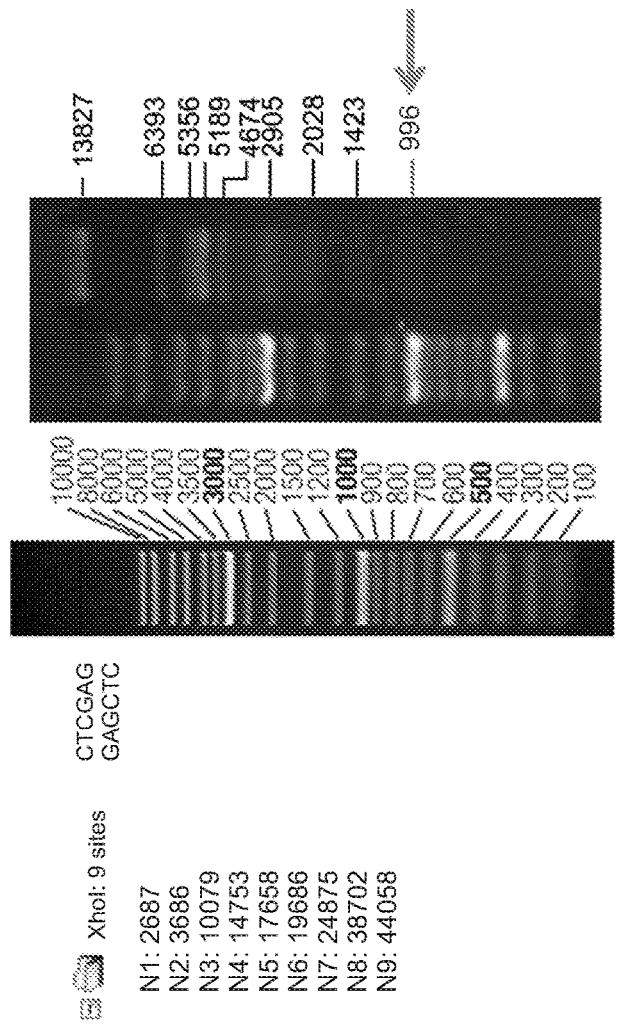
FIG. 4B is an agarose gel wherein DNA fragments of the FAdV-9 recombinant virus with a HN protein insert of the Newcastle's disease are shown, built according to the present invention, obtained by restriction enzyme digestion.
Figure 4C:
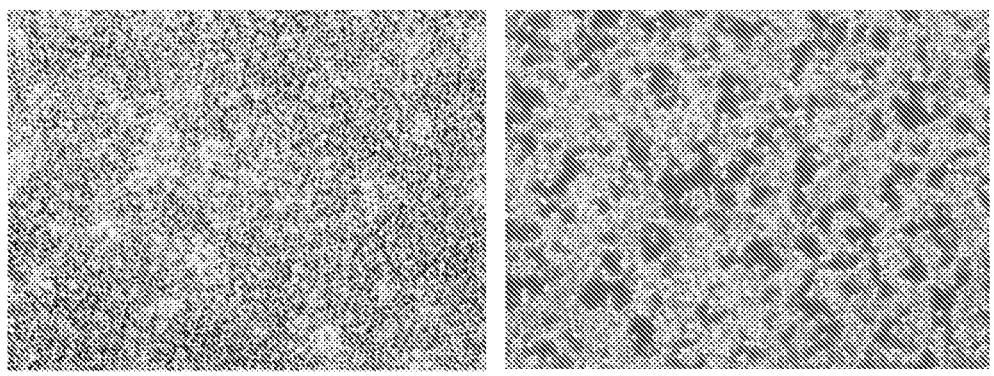
FIG. 4C is a non-infected CeLi cell culture, and one infected with a FAdV-9 recombinant virus with an HN protein insert of the Newcastle's disease, built according to the present invention

During the development of the present invention, it has been found that a recombinant vaccine comprising a serotype-9 fowl adenovirus vector (FAdV-9) having at least one exogenous nucleotide sequence inserted encoding for at least one disease antigen of interest, and which replaces the genome non-essential region of the adenovirus, specifically located between the 491-2782 nucleotides, and a pharmaceutically acceptable carrier, adjuvant and/or excipient, affords suitable protection against said disease of interest, resulting also stable when produced at an industrial scale, since the adenovirus vector does not lose the exogenous nucleotide sequence inserted when carrying out the successive passes in cell cultures. Likewise, it is surprising that this recombinant vaccine does not lose efficacy in vaccinated birds even if administered in combination with a Marek's disease whole virus vaccine, and that neither the Marek's vaccine loses efficacy when administered with this recombinant vaccine. In the same way, the recombinant vaccine of the present invention presents the advantage that its effectiveness is not affected by maternal antibodies in newborn animals and provides, with only one application, early and lasting protection.

In this sense, for the purposes of this invention it is considered that early protection is the one achieved within 19 days starting from the application of the vaccine, whereas lasting protection is the one achieved up to at least 90 days after application of the vaccine.

The adenovirus vector used may be alive (i.e., live or active) or inactivated. The term alive, live, or active means that the recombinant vector maintains its replication ability, while inactivated means that the adenovirus recombinant vector having the exogenous nucleotide sequence has lost the replication ability. Deactivation (i.e., inactivation) of the recombinant vector is performed utilizing physical or chemical procedures which are well known in the state of the art, such as chemical deactivation with formaldehyde or beta-propiolactone (Office International des Epizooties 2008). Newcastle Disease. OIE Manual of Diagnostic Tests and Vaccines for Terrestrial Animals. Office International des Epizooties. France, p. 576-589.

As mentioned above, the vector used is a serotype-9 fowl adenovirus (FAdv-9) which includes any strain. Preferably, FAdV-9 is selected from strains with GenBank accession numbers EU979376, AF083975, HQ697356, AF508958, AF339923, EU847634, EU847629, EU847628, DQ323986, AY683550, EU847635, NC_000899, and AC_000013.

Now, regarding the exogenous nucleotide sequence, it encodes for at least on antigen of a disease of interest, preferably said antigen being of at least one disease selected from avian influenza, hepatitis with inclusion bodies, birds infectious laryngotracheitis, Newcastle's disease, bursa of Fabricius infection, infectious bronchitis, disease caused by metapneumovirus (MPNV), Marek's disease, birds infectious anemia or any other gen which size allows insertion in the adenovirus vector. More preferably, an avian influenza gen is utilized.

In a specific embodiment of the present invention, the exogenous nucleotide sequence consists of the gene encoding the group comprising hemagglutinin (HA) of the avian influenza virus, selected from the 18 hemagglutinin subtypes or immunogenic variant of influenza virus, which more preferably encodes at least one of the subtypes H1, H2, H3, H5, H6, H7 or H9 of said protein; fiber and hexon of the inclusion bodies hepatitis virus, serotypes 4 and 8; glycoprotein B (gB) and glycoprotein D (gD) infectious laryngotracheitis virus from birds (LTI); HN and F proteins of the virus of Newcastle's disease; VP2 protein virus infection of the bursa of Fabricius; S1 and S2 protein of the infectious bronchitis virus; F protein of metapneumovirus (MPNV); and VP1, VP2 and VP3 protein of infectious anemia in birds.

Likewise, the exogenous nucleotide sequence can comprise a gen encoding at least one antigen of a fowl adenovirus different from the FAdV-9 utilized as viral vector.

The vaccine adenovirus vector comprising the exogenous gene of interest of the present invention may be prepared by PCR amplification of the nucleotide sequence of interest, in order to be able to insert it afterwards, already amplified, inside the adenovirus vector in which the non-essential genome region located between 491-2782 nucleotides has been eliminated. The exogenous gene insertion and the deletion of the adenovirus non-essential region are made using standard cloning techniques in molecular biology. The infectious clone thus produced is transfected in a cell culture to generate the recombinant virus.

The virus replicates in any system suitable for its growth, such as immortalized liver cells of avian origin (CeLi), commercial cell lines or expressly designed for growing the adenovirus, until reaching at least the required virus concentration in order to achieve an antigenic response, preferably at least of $10^{5.0}$DICC 50% per dose, more preferably at least $10^{6.0}$DICC 50% per dose.

For example, the recombinant virus can replicate in CeLi line cells grown with a specific culture medium, utilizing static growth systems, in cell culture bottles, in micro carriers, in large scale cell production systems, or in Roller bottles systems, until a titer on immune peroxidase tests reaches a minimum of $10^{6.0}$DICC 50% per dose. This titration may be reached after carrying out from 5 to 10 blind passes in the same kind of cells. Further, the harvest may be centrifuged, fractioned and maintained frozen, thus obtaining the so-called master seed (MS)

With the master seed, a further pass is performed on the same cells for making the production seed (SP) and one more from this one for making vaccines.

Thus, the present invention includes a master seed of a serotype-9 avian adenovirus recombinant virus (FAdV-9) which has an exogenous nucleotide sequence inserted encoding a disease of interest antigen and replacing the adenovirus genome non-essential region, specifically located between 491-2782 nucleotides; said master seed is obtained after 6 to 11 passes in cell culture.

Now, in the embodiment where the vaccine is alive or active, it is an active virus, preferably selected from naturally apathogenic avian adenoviruses, of low pathogenicity or attenuated by procedures already known in the state of the art. On the other hand, when the vaccine is deactivated, once the required viral concentration to achieve the antigenic response is reached, it proceeds with the deactivation of the virus. Preferably, the deactivation is carried out through physical or chemical procedures well known in the state of the art, preferably through chemical deactivation by formaldehyde or beta-propiolactone.

In case the vaccine of the present invention is alive or active, the pharmaceutically acceptable vehicles are aqueous solutions, preferably selected from the group consisting of aqueous solutions comprising TPGA stabilizer (trehalose, phosphate, glutamate, albumin); aqueous solutions comprising peptone stabilizer; and aqueous solutions comprising skimmed milk.

When the vaccine of the present invention is deactivated, the pharmaceutically acceptable vehicles are preferably aqueous solutions or emulsions. More particularly, the vehicle used is preferably a water-oil, oil-water or water-oil-water (WOW) emulsion, preferably a water-oil-water emulsion.

Regarding administration of the alive or active vaccine, this can be performed intramuscularly, intranasally, subcutaneously, by aspersion, nebulization, orally through drinking water, or in ovo utilizing suitable means and ways in each case. If it is a deactivated vaccine, this is administered intramuscularly or subcutaneously, preferably subcutaneously.

Likewise, the recombinant vaccine of the present invention can be administered in a single dose, in two doses or more, either alone or jointly with other recombinant or non-recombinant vaccines, alive (active) or deactivated, such as the vaccine against Marek's disease.

Likewise, even when the vaccine of the present invention is administered in a single dose or application, it achieves both early and lasting protection for the disease of interest related to the antigen encoded by the exogenous nucleotide sequence inserted in the viral vector contained in said vaccine.

In an additional embodiment, a multivalent recombinant vaccine comprising a vector of serotype-9 fowl adenovirus (FAdV-9) according to the present invention, having at least two exogenous nucleotide sequences inserted encoding at least two antigens either from the same disease of interest or different diseases of interest, and replacing the genome non-essential region of the adenovirus, specifically located between 491-2782 nucleotides is described.

In an embodiment of the present invention, a multivalent vaccine comprising a first vaccine based on a vector of serotype-9 avian adenovirus (FAdV-9) according to the present invention, having at least one exogenous nucleotide sequence inserted encoding at least one antigen of a disease of interest and replacing the genome non-essential region of the adenovirus, specifically located between 490-2782 nucleotides is described; and at least a second vaccine based on a vector of serotype-9 fowl adenovirus (FAdV-9) according to the present invention, having at least one exogenous nucleotide sequence encoding at least one antigen different from that of the first vaccine, either of the same disease of interest or a different one, and replacing the genome non-essential region of the adenovirus, specifically located between 491-2782 nucleotides. The multivalent vaccine may be found in alive or active, or deactivated forms.

Likewise, the present invention contemplates a multivalent vaccine comprising a Marek's disease whole virus vaccine in combination with at least one vaccine based on a serotype-9 fowl adenovirus vector (FAdV-9) according to the present invention, having an exogenous nucleotide sequence inserted encoding for a disease antigen of interest and which replaces the adenovirus genome non-essential region, specifically located between the 491-2782 nucleotides. The multivalent vaccine may be found in alive or active, or deactivated forms.

Further, in another aspect of the invention, a vaccination method against diseases in animals is disclosed, which comprises supplying to an animal a recombinant vaccine according to the present invention, comprising a serotype-9 fowl adenovirus vector (FAdV-9) having an exogenous nucleotide sequence inserted encoding for a disease antigen of interest, and which replaces the adenovirus genome non-essential region, specifically located between the 491-2782 nucleotides; and a pharmaceutically acceptable vehicle, adjuvant and/or excipient; wherein said vaccine is able to generate an immune-response in animals.

The exogenous nucleotide sequence encodes an antigen of a disease of interest, preferably from at least one disease selected from avian influenza, hepatitis with inclusion bodies, birds infectious laryngotracheitis, Newcastle's disease, bursa of Fabricius infection, infectious bronchitis, disease caused by metapneumovirus (MPNV), Marek's disease, birds infectious anemia or any other gen which size allows insertion in the adenovirus vector. Preferably, an avian influenza antigen is used.

Preferably, the exogenous nucleotide sequence consists of the gene encoding the group comprising hemagglutinin (HA) of the avian influenza virus, selected from the 18 hemagglutinin subtypes or immunogenic variant of the influenza virus, which more preferably encodes at least one of the subtypes H1, H2, H3, H5, H6, H7 or H9 of said protein; fiber and hexon of the inclusion bodies hepatitis virus, serotypes 4 or 8; glycoprotein B (gB) and glycoprotein D (gD) of the infectious laryngotracheitis virus from birds; HN and F proteins of the virus of Newcastle's disease; VP2 protein virus infection of the bursa of Fabricius; S1 and S2 protein of the infectious bronchitis virus; F protein of metapneumovirus (MPNV); and VP1, VP2 and VP3 protein of birds infectious anemia.

Likewise, the required concentration of the recombinant vaccine in order to achieve suitable protection is of at least $10^{5.0}$DICC 50% per dose, more preferably of at least $10^{6.0}$DICC 50% per dose.

The alive or active recombinant vaccine can be administered intramuscularly, intranasally, subcutaneously, by aspersion, nebulization, orally through drinking water, or in ovo utilizing suitable means and ways in each case. If it is a deactivated vaccine, this is administered intramuscularly or subcutaneously, preferably subcutaneously. Likewise, the recombinant vaccine of the present invention can be administered in a single dose or in two or more doses, either alone or in combination with other recombinant or non-recombinant vaccines, alive (active) or deactivated, such as the vaccine against Marek's disease.

Likewise, even when the vaccine of the present invention is administered in a single dose or application, it achieves both early and lasting protection for the disease of interest related to the antigen encoded by the exogenous nucleotide sequence inserted in the viral vector contained in said vaccine.

The present invention will be better understood from the following examples, which are shown for illustrative purposes only to allow proper understanding of the preferred embodiments of the present invention, without implying that there are no other embodiments non-illustrated which may be practiced based on the above disclosed detailed description.

EXAMPLES

Example 1. Generation of an FAdV-9 Vector

Firstly, a FAdV-9 45 kb genome comprising SEQ ID NO: 1, generated by reverse genetics and containing regions FV1 (comprised between the 1-491 nucleotides) and FV2 (comprised between the 2,782-7,453 nucleotides), had its non-essential region of 2,291 pb removed, comprised between the 491-2,782 nucleotides, i.e., at the 5' end of the genome; Further, a SwaI site, unique for the genes of interest, was inserted at the 491 site. This genome was sub-cloned in the pBg plasmide to acquire the unique restriction sites at its ends to allow the generation of the alive virus in a culture.

Further, an EcoRV site was introduced in FV-2 using an oligonucleotide by the PCR technique, thus obtaining the intermediate pAL2.4. In this intermediate, an original genome fragment comprised between the 4,391 and 7,453, nucleotides was deleted, remaining a recombinant arm of 2,100 pb. Further, the fragment of PCR EcoRV-EcoRV was cloned shunted in pShuttle from AdEASY, excising with EcoRV-PmeI. The EcoRI site was kept.

In the SwaI site at the 491 nucleotide, an expression cassette from pVAX was cloned using CMV, poliLinker and PoliA, and which also contained a PmeI site unique to clone the gene of interest, thereby obtaining the infectious clone of interest. The transfection of the infectious clone in cell culture generates the recombinant virus of interest.

Example 2. Generation of an rFAdV9-435 Recombinant Virus rFAdV9-435 in Cell Culture According to the methodology described in Example 1, an FAdV-9 infectious clone with insertion of the H5 gene from low pathogenicity avian influenza virus VIABP-H5N2, strain 435 (rFAdV9-435) was obtained, with GenBank accession number FJ864690, and which comprises the sequence SEQ ID NO: 2.

Firstly, in order to obtain the master seed (SM), the rFAdV9-435 was replicated in CeLi line cells grown with DMEM F12+Glutamax culture medium, in cell culture bottles (static system). After performing 7 blind passes on the same cell type, a titer on immune peroxidase tests of $10^{6.0}$DICC 50% was reached. The harvest was centrifuged at 500 g for 20 minutes, and it was fractioned in 1.5 mL cryovials, which were kept in deep freezing at a temperature between −70° C. and −80° C.

Tests were made to the SM to exclude the presence of bacteria, avian mycoplasma, fungi and yeasts, as well as to prove that said MS was avian virus-free.

Further, the SM was tested in specific pathogen-free chickens (SPF) in order to determine its innocuousness, power, immunogenicity and the minimum dose required to generate a suitable protection and immunogenicity.

A further pass was performed with the master seed on the same cells (CeLi) for making the production seed.

Example 3. Generation of Other Recombinant Viruses

Following the same methodology described above, additional FAdV-9 recombinant viruses were obtained according to what is shown in Table 1:

TABLE 1

FAdV-9 recombinant viruses generated with different inserts.

| Insert | Name of the recombinant virus |
|---|---|
| Avian influenza H7 H7N3 | rFAdV9-H7IA |
| Fiber of hepatitis with serotype-4 inclusion bodies | rFAdV9-Fib HCl |
| Avian laryngotracheitis glycoprotein B (gB) | rFAdV9-gBLT |
| Newcastle's disease HN | rFAdV9-HN |
| Infectious bronchitis S1 and S2 | rFAdV9-S1S2BI |
| Avian influenza H5 and H7 | rFAdV9-H5H7IA |
| Porcine circovirus ORF2 | rFAdV9-ORF2PCV2 |
| Avian infectious anemia VP1 and VP2 | rFAdV9-VP2VP1CAV |
| Avian laryngotracheitis glycoprotein D (gD) | rFAdV9-gDLT |
| *Salmonella enterica* flagellin C | rFAdV9-FliC |

These recombinant vectors were characterized by XhoI digestion. In FIG. 1A the DNA restriction map of the rFAdV9-H7IA recombinant vector is shown; the 4.7 kb band shows the restriction fragment where the heterologous gene is cloned. In FIG. 1B a 3629 bp can be observed, which corresponds to the avian influenza HA gene, demonstrating that the rFAdV9-H7IA recombinant vector indeed has this gene inserted and, furthermore, said vector is stable after 10 passes in cell culture. In FIG. 1C, on the left side, a non-infected CeLi cell culture can be observed, whereas on the right side the cytopathic effect caused by propagation of the rFAdV9-H7IA recombinant vector in CeLi cells with a viral titer of $1.1\times10^6$ UFP can be observed, indicating that it generates a good cytopathic effect due to the fact that said recombinant vector behaves stably and normally in CeLi cell culture.

Further, in FIG. 2A the DNA restriction map of the rFAdV9-Fib HCl recombinant vector is shown; the 1.4 kb band shows the restriction fragment where the heterologous gene is cloned, while in FIG. 2B is 1652 pb band, corresponding to Fib4 gene of hepatitis with serotype-4 inclusion bodies is seen, showing that the rFAdV9-Fib HCl recombinant vector indeed has this gene inserted and further that said vector is stable after 10 passes in cell culture. Finally, in FIG. 2C, on the left side, a non-infected CeLi cell culture can be observed, whereas on the right side the cytopathic effect caused by propagation of the rFAdV9-Fib HCl recombinant vector in CeLi cells with a viral titer of $1.4\times10^5$ UFP can be observed, indicating that it generates a good cytopathic effect due to the fact that said recombinant vector behaves stably and normally in CeLi cell culture.

In FIG. 3A the DNA restriction map of the rFAdV9-gBLT recombinant vector is shown; the 5.6 kb band shows the restriction fragment where the heterologous gene is cloned. FIG. 3B shows a 4,573 pb band, corresponding to the gB gene of birds infectious laryngotracheitis, demonstrating that the rFAdV9-gBLT recombinant vector indeed has this gene inserted and that said vector is stable after 10 passes in cell culture. In FIG. 3C, on the left side a non-infected CeLi cell culture can be observed, whereas on the right side the cytopathic effect caused by propagation of the rFAdV9-gBLT recombinant vector in CeLi cells with a viral titer of $2.6\times10^6$UFP can be observed. The above indicates that this recombinant vector is stable in CeLi cell culture.

In FIG. 4A the DNA restriction map of the rFAdV9-HN recombinant vector is shown; the 4.8 kb band shows the restriction fragment where the heterologous gene is cloned. FIG. 4B shows a 996 bp band, corresponding to the HN gene of Newcastle's disease, with which it is shown that the rFAdV9-HN recombinant vector indeed has this gene inserted and that said vector is stable after 10 passes in cell culture. In FIG. 4C, on the left side, a non-infected CeLi cell culture can be observed, whereas on the right side the cytopathic effect caused by propagation of the rFAdV9-HN recombinant vector in CeLi cells with a viral titer of $1.3\times10^6$UFP can be observed. The above indicates that this recombinant vector is stable in CeLi cell culture.

Example 4. Generation of an FAdV-9 Recombinant Vector According to Other Known Adenoviral Vectors The FAdV-9 of 45 kb genome was cloned in plasmid pWE-15; this genome has two repeating blocks in tandem called TR-1 (located between the 37,648 and 37,812 nucleotides) and TR-2 (located between the 38,707 and 40,561 nucleotides, i.e., between 0.0023 and 0.0039 in (60 and 100 mu) at the 3' end, which are not required for its viral replication. After that, this genome in pWE-15 was subcloned in plasmide pBg in order to add the PacI sites at the genome ends which are useful to linearize the DNA during the virus generation in cell culture.

In order to generate the intermediate, the TR-2 region was amplified by PCR and cloned in the bacterial plasmid pTRE-2 with the unique I-CeuI and PI-SceI sites at both ends. Afterwards, an expression cassette was inserted, containing a CMV-polilinker to direct the Newcastle's disease virus HN gene expression, thus obtaining the infectious clone pFΔTR2-CMV HN.

The rFΔTR2-CMV HN recombinant virus was obtained through transfection of the infectious clone in CeLi cell culture.

Figure 5A:
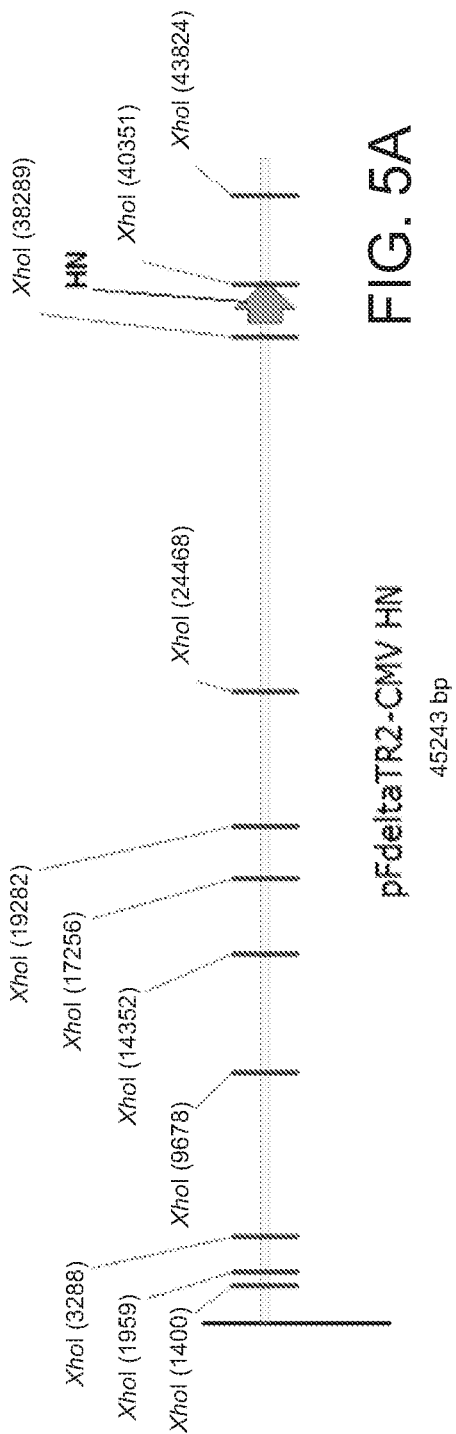
FIG. 5A is the DNA restriction map of the FAdV-9 recombinant virus with a HN protein insert of the Newcastle's disease virus, inserted between the 38,807 and 40,561 nucleotides of the genome.
Figure 5B:
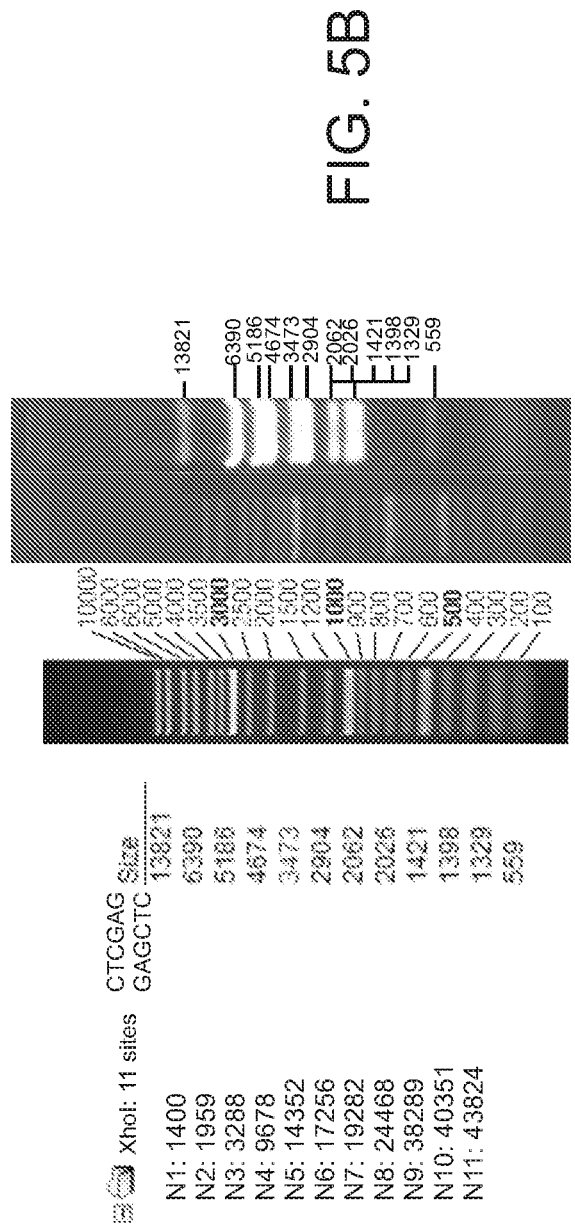
FIG. 5B is an agarose gel in which DNA fragments of the FAdV-9 recombinant virus with an HN protein insert of the Newcastle's disease virus, inserted between the 38,807 and 40,561 nucleotides of the genome, obtained by restriction enzyme digestion are shown.
Figure 5C:
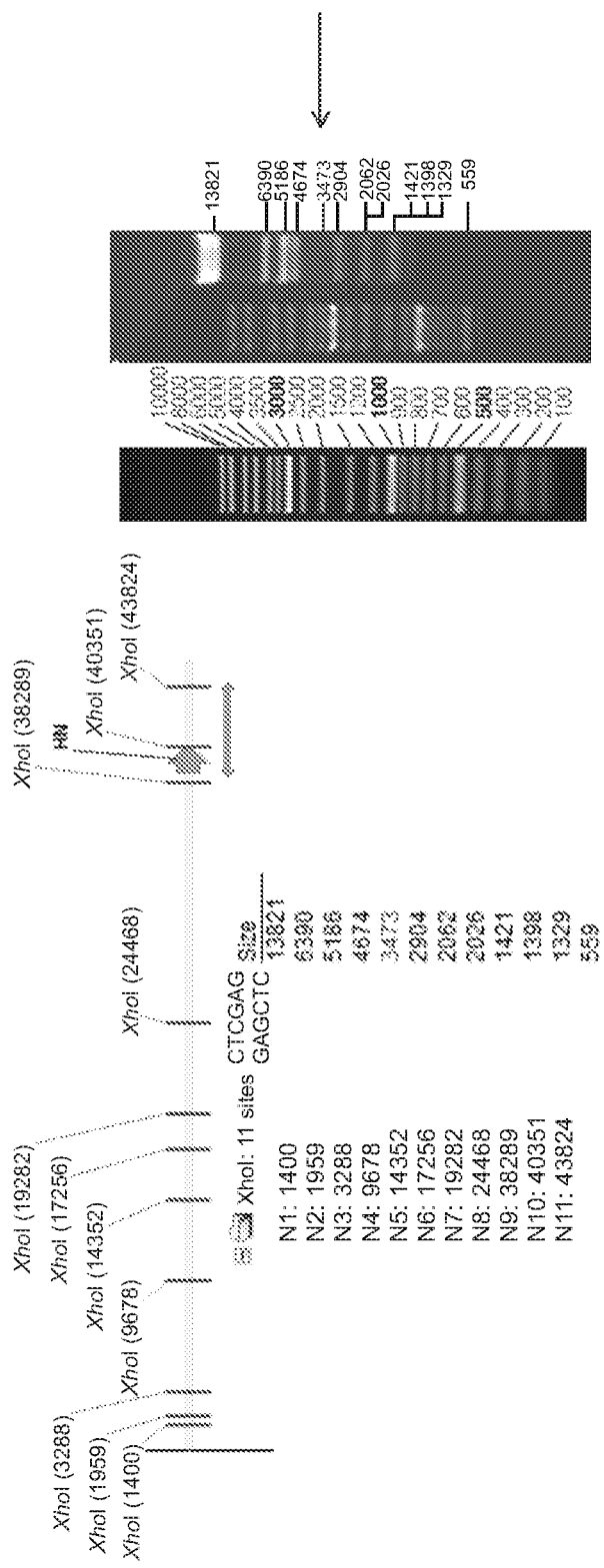
FIG. 5C is an agarose gel in which DNA fragments of the FAdV-9 recombinant virus with an HN protein insert of the Newcastle's disease virus, inserted between the 38,807 and 40,561 nucleotides of the genome after 2 passes in CeLi cell culture, obtained by restriction enzyme digestion, are shown.
Figure 6:
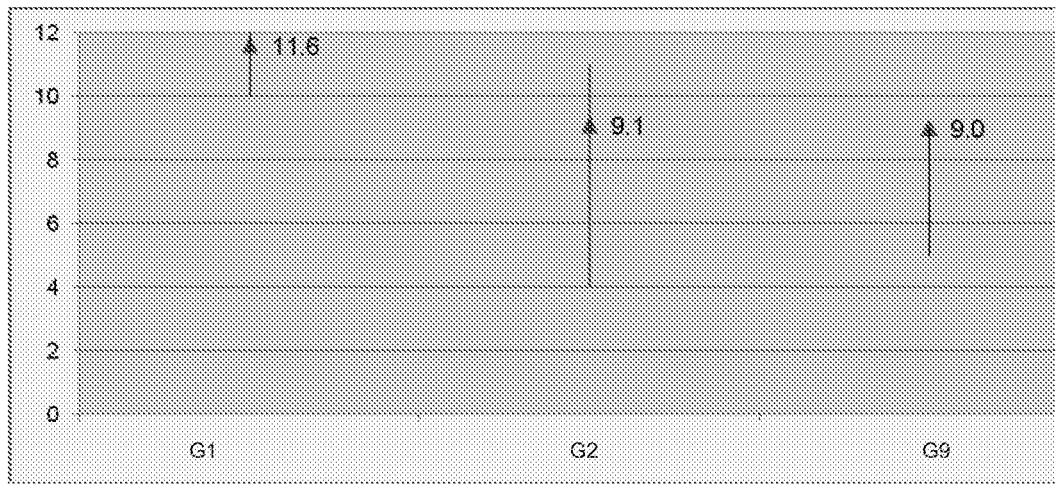
FIG. 6 is a graph showing the results of hemagglutination inhibition (IH) of light breed commercial chicks (CRL) immunized in-ovo, with sera taken at the age of 1 day (DE).
Figure 7:
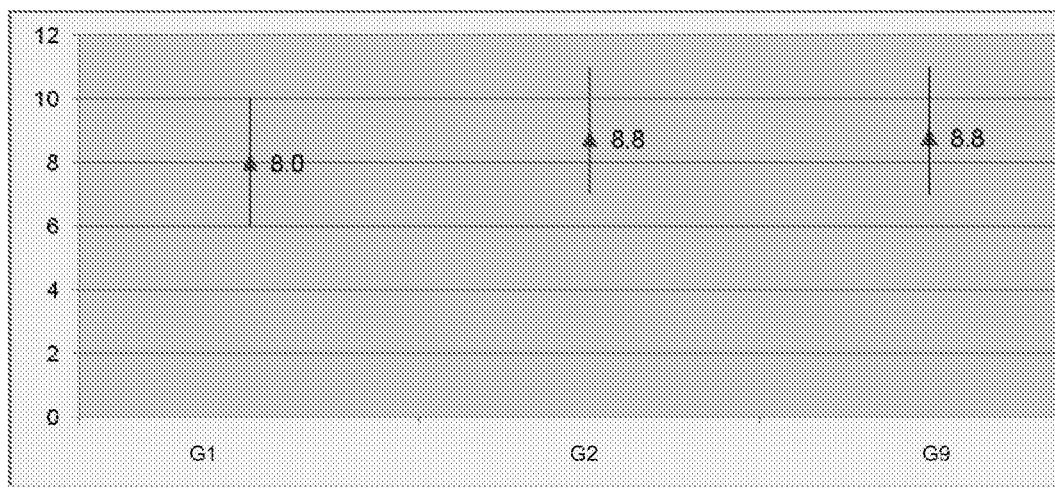
FIG. 7 is a graph showing the IH results of CRL chicks immunized in ovo, with sera taken at 10 DE.
Figure 8:
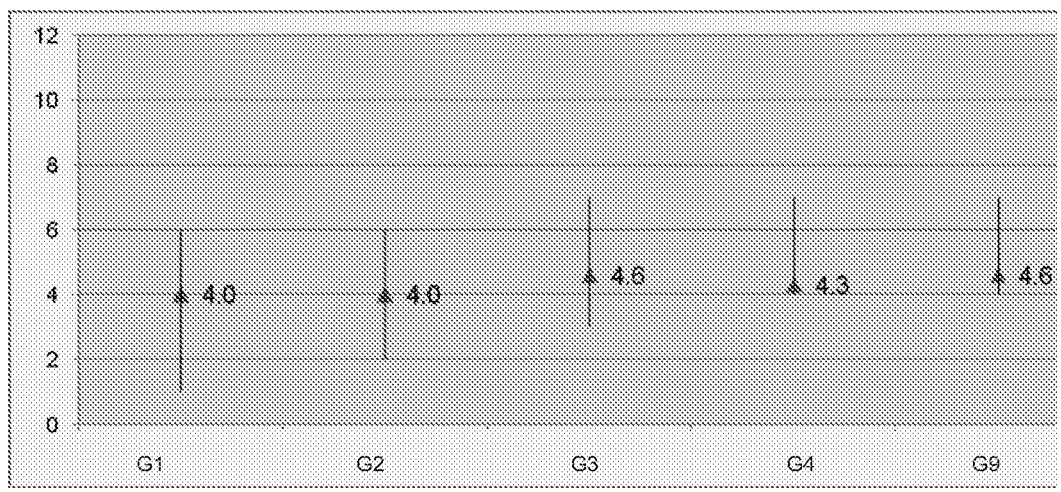
FIG. 8 is a graph showing the IH results of CRL chicks immunized in ovo after 18 days of incubation (DI) or at 1 DE, with sera taken at 19 DE.
Figure 9:
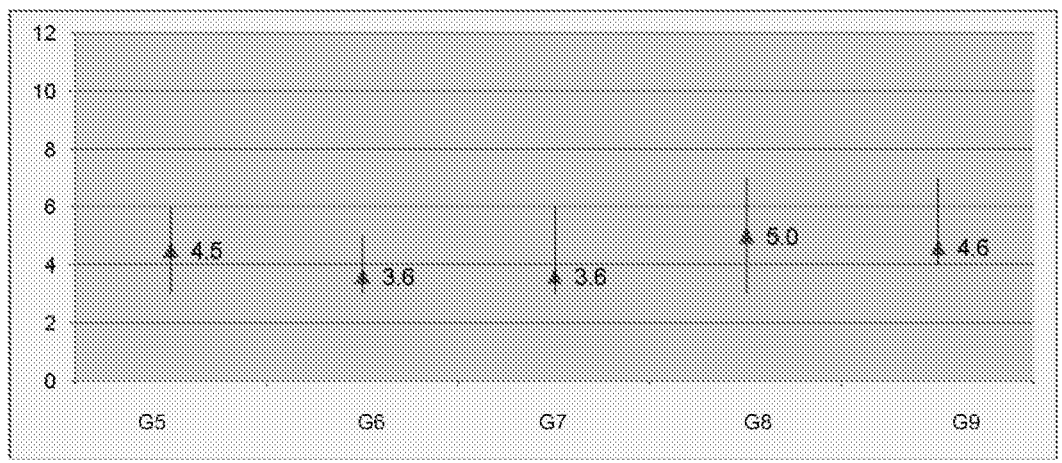
FIG. 9 is a graph showing the IH results of CRL chicks immunized in ovo at 18 DI or at 1 DE, and re-vaccinated at 10 DE with sera taken at 19 DE.
Figure 10:
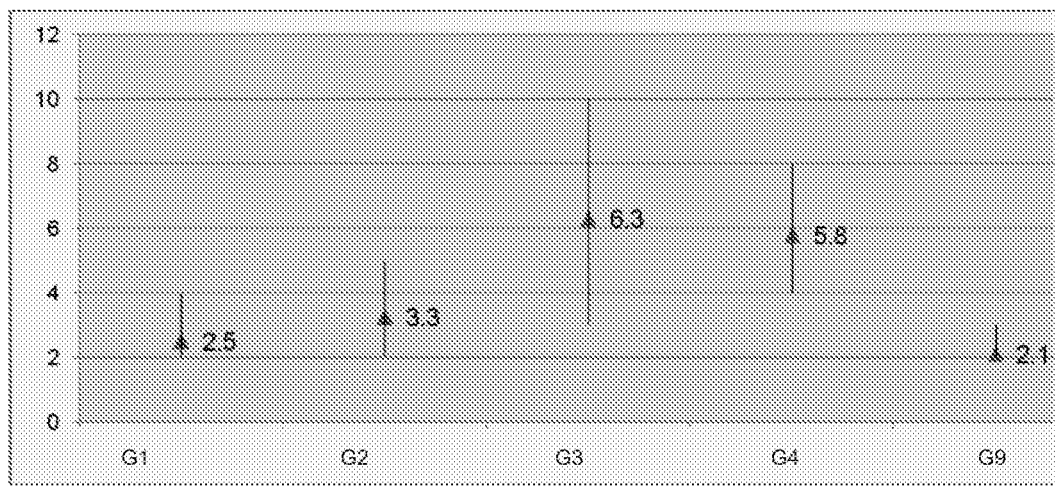
FIG. 10 is a graph showing the IH results of CRL chicks immunized in ovo at 18 DI or at 1 DE, with sera taken at 31 DE.
Figure 11:
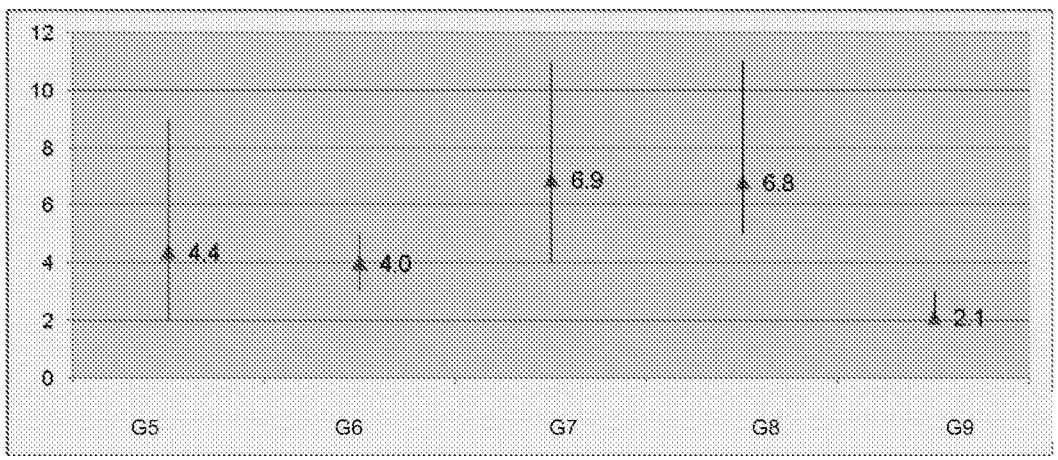
FIG. 11 is a graph showing the IH results of CRL chicks immunized in ovo at 18 DI or at 1 DE, and re-vaccinated at 10 DE with sera taken at 31 DE.
Figure 12:
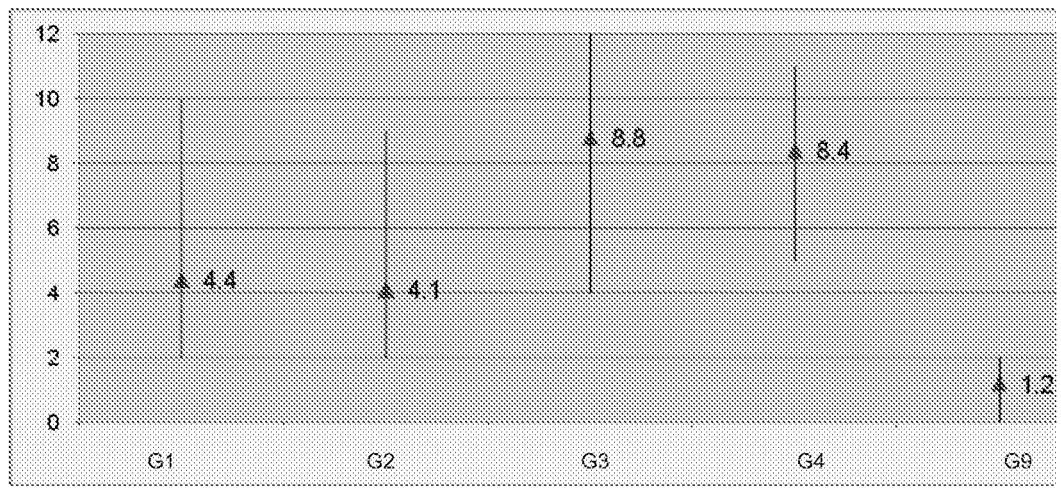
FIG. 12 is a graph showing the IH results of CRL chicks immunized in ovo at 18 DI or at 1 DE, with sera taken at 38 DE.

In FIG. 5A it is possible to observe the DNA restriction map of the rFΔTR2-CMV HN recombinant vector; the 3,473 kb band shows the restriction fragment where the heterologous gene is cloned. FIG. 5B shows a DNA digestion band with XhoI, indicating the 3,473 bp, corresponding to the HN gene of the Newcastle's disease virus, with which it is demonstrated that the rFΔTR2-CMV HN recombinant vector indeed has this gene inserted. Nonetheless, in FIG. 5C it can be observed that the 3,473 bp band corresponding to the HN gene has disappeared after 2 passes in CeLi cell culture, with a viral titer of $1.1 \times 10^4$ UFP, which demonstrates that the rFΔTR2-CMV HN vector lost the exogenous gene insert with the passes in cell culture, thereby resulting unstable and unsuitable for industrial production of recombinant vaccines.

Example 5. Production Method of a Vaccine Active with FAdV-9 Recombinant Virus with H5 Insert of Avian Influenza: rFAdV9-435

CeLi line cells were cultured steadily in a Roller system. To this end, a pass 32 vial from the Working Cell Bank (BCT) was thawed in a T25 vial. 3 consecutive passes were made with a 1:3 ratio, each 2-3 days in order to recover to growing speed (TD=24 hours). Once the growth speed was recovered, cells were propagated in a T75 and T225 box (1:3 ratio) and when an 80% confluence was obtained, they were infected with the production seed obtained in accordance to Example 2 with an infection multiplicity (moi) of 0.1DICC 50%/mL. At 5 days post-infection, the vials with their content were frozen at −70° C. during 24 hours. Then, they were thawed, the contents was recovered and centrifuged at 500 g during 20 minutes. It was packaged according to the produced volume.

The harvest was titrated by immune peroxidase, and it was formulated by adding harvested fluid, plus TPGA cbp as a stabilizer, in order to reach $10^{5.3}$DICC 50%/dose. The experimental vaccine was kept frozen at a temperature between −20° C. and −30° C. until use.

Example 6. In Vivo Assessment of the rFAdV9-435 Recombinant Active Vaccine Applied with or without Vaccine Against Marek's Disease A study was carried out with the purpose of determining the effectiveness of the active vaccine of the present invention and demonstrate that it is neither affected nor affects when administered to birds in combination with a vaccine against Marek's disease. The vaccine was administered in ovo and subcutaneously.

To that end, 270 1 day old (DE) Leghorn light breed commercial chicks (CRL) were employed, divided into 9 groups of 30 chicks each, in accordance to what is shown in Table 2.

The rFAdV9-435 active vaccine was applied in ovo after 18 days of incubation (DI) via allantois cavity (Ai) with a rate of $10^{6.1}$DICC 50%/0.2 mL alone for groups 2 and 6, and mixed and applied in combination with the vaccine against Marek strain HVT for groups 1 and 5 On the other hand, experiments were performed applying the vaccine a day after birth (DE), subcutaneously (SC) on the middle and upper portion of the neck for immunization with the rFAdV9-435 vaccine at a rate of $10^{6.1}$DICC 50%/0.2 mL. The vaccine alone was administered for groups 4 and 8; and mixed and applied in combination with a vaccine against Marek strain HVT for groups 3 and 7. Finally, at 10 DE groups 5 to 8 were re-vaccinated SC with $10^{6.5}$DICC 50%/0.5 mL of the rFAdV9-435 vaccine.

TABLE 2

Treatment groups with the rFAdV9-435 vaccine.

| Group | Vaccines | Application days and vaccines administration routes | | | Challenges with VIAAP-H5N2 days after birth (DE) | | |
|---|---|---|---|---|---|---|---|
| | | 18-DI | 1-DE | 10-DE | 19 DE | 31 DE | 45 DE |
| G1 | rFAdV9-435 + HVT | Ai | | | 10 | 10 | 10 |
| G2 | rFAdV9-435 | Ai | | | 10 | 10 | 10 |
| G3 | rFAdV9-435 + HVT | | SC | | 10 | 10 | 10 |
| G4 | rFAdV9-435 | | SC | | 10 | 10 | 10 |
| G5 | rFAdV9-435 + HVT + rFAdV9-435 | Ai | | SC | 10 | 10 | 10 |
| G6 | rFAdV9-435 + rFAdV9-435 | Ai | | SC | 10 | 10 | 10 |
| G7 | rFAdV9-435 + HVT + rFAdV9-435 | | SC | SC | 10 | 10 | 10 |
| G8 | rFAdV9-435 + rFAdV9-435 | | SC | SC | 10 | 10 | 10 |
| G9 | Control (not vaccinated) | — | — | — | 10 | 10 | 10 |

Animals were housed in isolation units, where they were challenged at 19, 31 and 45 DE subdividing the groups into three subgroups of 10 chicks each, for each challenge.

The challenge virus was a high pathogenicity avian influenza virus, VIAAP-H5N2, strain A/chicken/Querétaro, which was adjusted with PBS to pH 7.2, in order to apply $10^{7.5}$DIEP50% in 0.3 mL to each chicken, volume that each chicken received applying 0.06 ml (two drops) on each eye and 0.09 ml (3 drops) in each nostril.

Example 6A. Potency Assessment

All groups were observed daily during 10 days after the challenges to assess the clinic data; each chicken was individually checked and scored with a numeric value according to the data in Table 3.

TABLE 3

Daily evaluation of the clinic data post-challenges with VIAAP-H5N2.

| Clinic signs | Mild | Severe |
|---|---|---|
| Conjunctivitis | 1 | 2 |
| Conjunctivitis + ruffled feathers | 3 | 4 |
| Conjunctivitis + ruffled feathers + lethargy | 5 | 6 |
| Death | 7 | — |

The maximum value for the clinical data severity (MCDS) of each experimental group corresponded to the average of the individual value addition. The mortality (M) was estimated in an accumulated basis during the 10 observation days, adjusting the maximum value of the clinic signals at 100%.

The maximum morbidity of the group (MM) equals the maximum percentage of sick birds in one of the 10 observation days. The morbidity index (IMb) was calculated as follows:

$$IMb = \frac{(SMCC)(MM)}{100}$$

For example:

$$IMb = \frac{(56\%)(80\%)}{100}$$

$$IMb = 44.8\%$$

The results of protection towards mortality (PM) and IMb on chickens challenged with VIAAP-H5N2 at 19, 31 and 45 DE are presented in Table 4.

TABLE 4

Potency results in CRL chicks vaccinated with rFAdV9-435 and challenged with VIAAP-H5N2.

| | PM (%) | | | IMb (%) | | |
|---|---|---|---|---|---|---|
| Group | 19 DE | 31 DE | 45 DE | 19 DE | 31 DE | 45 DE |
| G1 | 90 | 100 | 100 | 16.8 | 12.7 | 8.2 |
| G2 | 90 | 100 | 100 | 26.7 | 6.5 | 7.1 |
| G3 | 100 | 100 | 100 | 3.9 | 1.5 | 1.0 |
| G4 | 100 | 100 | 100 | 1.2 | 1.2 | 0.9 |
| G5 | 100 | 100 | 100 | 9.1 | 9.7 | 7.6 |

TABLE 4-continued

Potency results in CRL chicks vaccinated with rFAdV9-435 and challenged with VIAAP-H5N2.

| | PM (%) | | | IMb (%) | | |
|---|---|---|---|---|---|---|
| Group | 19 DE | 31 DE | 45 DE | 19 DE | 31 DE | 45 DE |
| G6 | 100 | 100 | 100 | 10.2 | 8.8 | 5.0 |
| G7 | 100 | 100 | 100 | 0.1 | 1.2 | 0.6 |
| G8 | 100 | 100 | 100 | 0.5 | 0.6 | 0.1 |
| G9 | 0 | 0 | 0 | 100 | 100 | 100 |

As may be seen, the potency results confirm the efficacy of the rFAdV9-435 vaccine of the present invention for its use in controlling H5N2 avian influenza, and they suggest that it may be used to control other avian influenza subtypes.

Likewise, these results confirm that the mixture and application of the vaccine against Marek's disease does not interfere with the rFAdV9-435 active vaccine when applied in combination.

Example 68. Immunogenicity Assessment

The results of hemagglutination inhibition tests (IH) showed that the antibodies levels against the antigen (Ag) of VIA-435, of both vaccinated and control groups showed very high levels of maternal antibodies, of $2^{9.0}$ at $2^{9.3}$ in obtained birds sera at 1 DE (FIG. 6), and from $2^{8.6}$ to $2^{8.8}$, for the sera obtained at 10 DO (FIG. 7).

In the case of sera obtained at 19 DE from all the groups (both control and vaccinated groups, including those immunized in ovo or at DE with re-vaccination of rFAdV9-435 at 10 DE, the detected antibody levels ranged from $2^{3,6}$ to $2^{4.6}$ (FIGS. 8 and 9).

The above results show that the levels of the antibodies as detected correspond to the maternal antibodies which were non-induced by the vaccine administration rFAdV9-435. However, just as it was mentioned above, the PM conferred for the early challenge at 19 DE for the different groups was from 90% and 100%, which indicates that the effectiveness of the vaccine of the present invention was not affected by the maternal antibodies against VIA-435. Additionally, they suggest that it was able to stimulate a cell-type specific immune response, generating protection before the challenge, which matches the scientific literature pointing out that cell immunity is of importance for viral diseases control.

Further, as may be seen in FIG. 10 for sera obtained at 31 DE, results indicate that groups immunized in ovo did not present a detectable antibody response for the IH test, whereas for groups immunized at DE antibody levels attributable to the rFAdV9-435 vaccine were detected with a titer of $2^{6.3}$ and $2^{5.8}$ for groups 5 and 6, in contrast with the non-vaccinated control group which resulted in a mean of $2^{2.1}$.

As shown in FIG. 11, in the case of groups immunized in ovo with re-vaccination at 10 DE, moderate levels of vaccine rFAdV9-435-induced antibodies were detected, with a titer of $2^{4.4}$ and $2^{4.0}$ for groups 5 and 6, respectively. Comparatively, the non-vaccinated control group resulted in an IH antibodies titer mean of $10^{2.1}$, which is technically considered as negative titers. In the case of groups immunized at DE, with re-vaccination at 10 DE, the result was of $2^{6.9}$ and $2^{6.8}$ for groups 7 and 8 respectively, suggesting that an anamnestic immune response was present.

In the case of the sera obtained at 38 D the results in FIG. 12 indicate, for groups immunized in ovo, that the rFAdV9-

435 vaccine for the first time allowed for detection of said antibody groups against VIA-435 Ag; more specifically, for group 1 of $2^{4.4}$ and for group 2 of $2^{4.1}$. On the other hand, for groups immunized at DE, the antibody levels resulted in a titer of $2^{8.8}$ and $2^{8.4}$ for groups 3 and 4, respectively, in contrast with the non-vaccinated control group which resulted in a mean of $2^{1.2}$.

Figure 13:
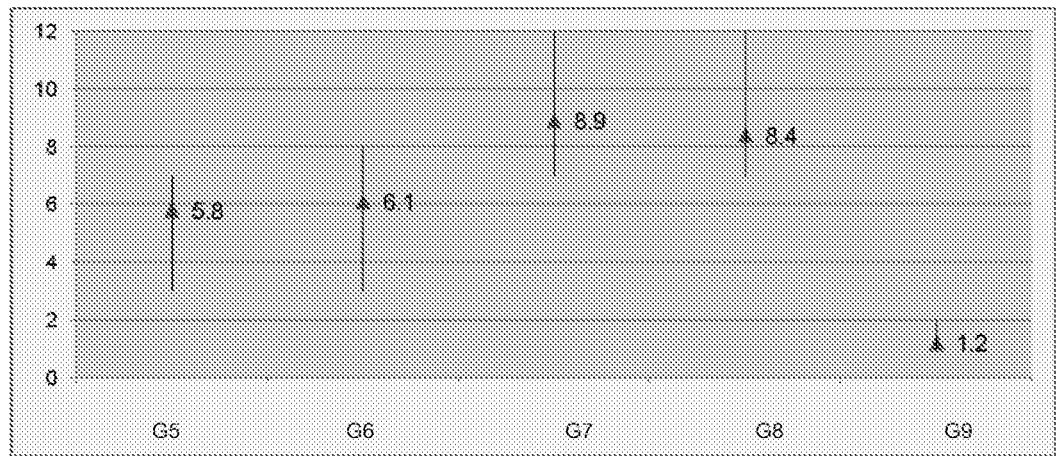
FIG. 13 is a graph showing the IH results of CRL chicks immunized in ovo at 18 DI or at 1 DE, and re-vaccinated at 10 DE with sera taken at 38 DE.

Whereby it refers to groups immunized in ovo with re-vaccination at 10 DE (FIG. 13), levels of induced antibodies were detected for the rFAdV9-435 vaccine, with a titration of $2^{5.5}$ and $2^{6.1}$ for groups 3 and 4, respectively, comparatively to the non-vaccinated, control group which resulted with a mean of $10^{1.2}$. In the case of groups immunized at DE, with re-vaccination at 10 DE, the result was of $2^{8.9}$ and $2^{8.4}$ for groups 7 and 8, respectively, which indicates that even at 38 DE the antibody level kept rising for all the groups.

Figure 14:
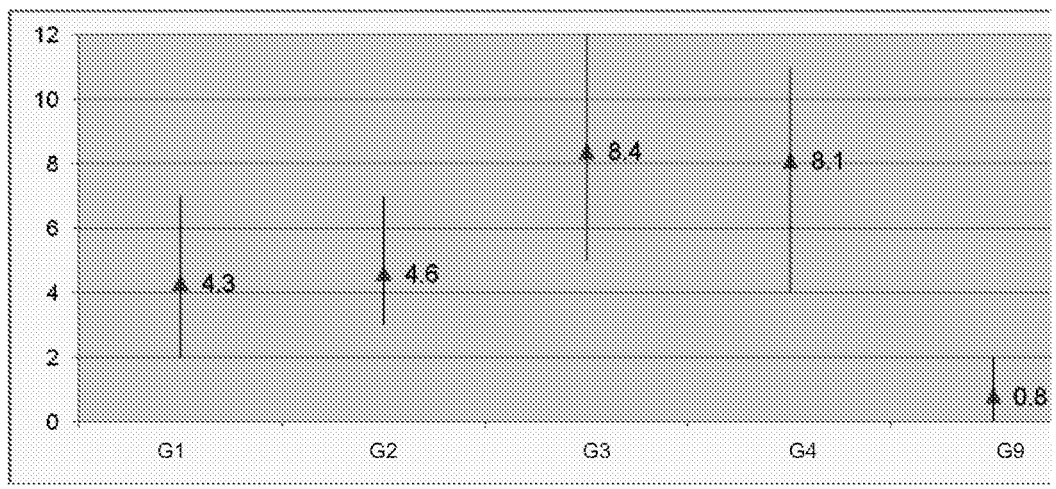
FIG. 14 is a graph showing the IH results of CRL chicks immunized in ovo at 18 DI or at 1 DE, with sera taken at 45 DE.

Finally, for the sera obtained at 45 DO, the results indicate, as may be appreciated in FIG. 14, for groups immunized in ovo, that the rFAdV9-435 vaccine allowed for detection of antibodies against VIA-435 Ag, for group 1 of $2^{4.3}$ and for group 2 of $2^{4.8}$, whereas for groups 3 and 4 the antibody levels resulted in a titer of $2^{8.4}$ and $2^{8.1}$, respectively, in contrast with the non-vaccinated control group which resulted in a mean of $2^{0.8}$.

Figure 15:
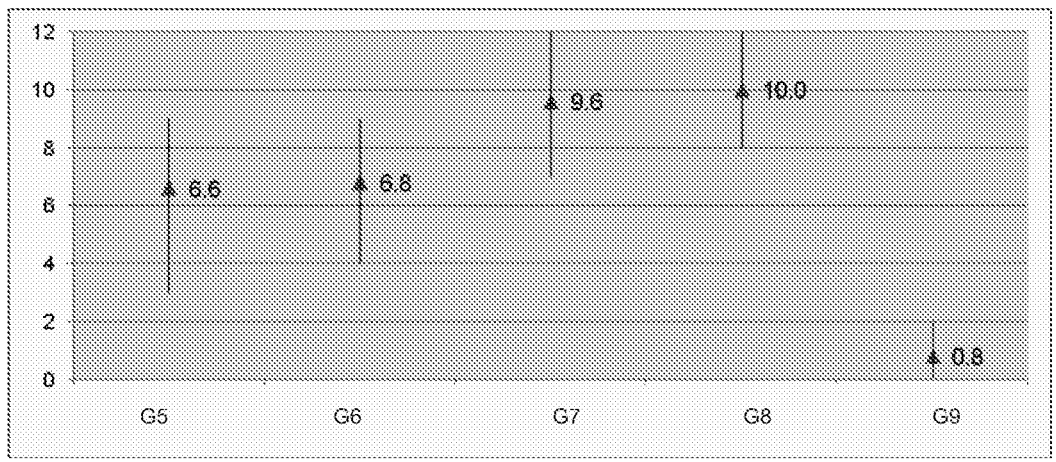
FIG. 15 is a graph showing the IH results of CRL chicks immunized in ovo at 18 DI or at 1 DE, and re-vaccinated at 10 DE with sera taken at 45 DE.

In groups immunized in ovo with re-vaccination at 10 DE (FIG. 15), levels of antibodies were detected induced by the rFAdV9-435 vaccine, with a titration of $2^{6.6}$ and $2^{6.8}$, for group 5 and group 6, respectively, comparatively to the non-vaccinated, control group which resulted with a mean of $10^{0.8}$. For the case of groups immunized at DE, with re-vaccination at 10 DE, the result was of $2^{9.6}$ and $2^{10.0}$ for groups 7 and 8, respectively; this indicates that even at 45 DE the antibody level remained at the same level for groups 5 and 6, whereas for groups 7 and 8 this antibody level kept increasing.

As can be observed from the above, these results indicate that the rFAdV9-435 vaccine, made according to the present invention, had the capacity to induce detectable antibody levels for the IH test, for groups vaccinated in ovo with detection starting from 31 DE for groups immunized in ovo and re-vaccination at 10 DE. While for groups vaccinated at DE, without re-vaccination, detection was also given starting from 31 DE, but with a titer higher than the one for the group vaccinated in ovo and re-vaccinated at 10 DE; for the group vaccinated at DE and re-vaccinated at 10 DE, the detected antibody levels did not reveal at this time an important anamnesic response.

Antibody levels for group 1 were detected for the first time at 38 DE (vaccination in ovo), and for group 3 (vaccination at DE) an increase in the antibody level is detected, which indicates that the rFAdV9-435 vaccine keeps increasing the humoral response even at 38 DE. Likewise, at 38 DE, for the group vaccinated in ovo with re-vaccination at 10 DE, an increase in the antibody level higher than that of the group that only received the in ovodose is noted; whereas for the group vaccinated at DE, with re-vaccination at 10 DE, the antibodies increase at 38 DE was not significant compared to the group that received only one dose at DE.

At 45 DE, both for the group with a single dose of vaccine in ovo and the group with a single dose of vaccine at DE, the antibody levels remained being practically the same as the 38 DE, which indicates that for these groups the maximum level of detectable circulating antibodies by an IH test was achieved at 38 DE. While for groups vaccinated in ovo and one day after birth, with re-vaccination at 10 DE, an important increase in antibody levels was still detected.

Example 7. In Vivo Assessment of the rFAdV9-435 Recombinant Active Vaccine Applied Alone or in Combination with a Vaccine Against Marek's Disease, with Challenge at 93 DE A second study was performed to determine the effectiveness of the active vaccine of the present invention.

The vaccine was administered via SC to 180 CRL chicks divided into 6 groups of 30 chicks each, in accordance to what is shown in Table 5; the HVT vaccine against Marek's disease utilized in combination with the vaccine of the present invention was a commercial vaccine with a titre of 4200 UFP/mL and it was employed according to the commercial laboratory indications.

For purposes of the following examples, it is considered that 1 chicken dose (DP) corresponds to the dose exponent in logarithmic scale administered to each bird, expressed in DICC 50%; for example, if one dose of $10^{7.1}$DICC 50% is administered, this is equivalent to 7.1 DP.

Animals were housed in isolation units, where they were challenged at 19, 31 and 93 DE ocularly and through the nostrils with 0.3 mL of VIAAP-H5N2 (strain A/chicken/Querétaro/14588-19/95), applying $10^{8.0}$DIEP50% in 0.3 mL to each chicken.

TABLE 5

Treatment groups with the rFAdV9-435 vaccine.

| Group | Vaccines | Application days, doses and vaccines administration route | | Challenges with VIAAP-H5N2 at different DE | | |
|---|---|---|---|---|---|---|
| | | 1 DE | 10 DE | 19 DE | 31 DE | 93 DE |
| G1 | rFAdV9-435 + HVT | SC (7.1 DP/0.2 mL) | | 10 | 10 | 10 |
| G2 | rFAdV9-435 | SC (7.1 DP/0.2 mL) | | 10 | 10 | 10 |
| G3 | rFAD9-435 | SC (7.1 DP/0.2 mL) | SC (7.5 DP/0.5 mL) | 10 | 10 | 10 |
| G4 | rFAdV9-435 | SC (6.1 DP/0.2 mL) | | 10 | 10 | 10 |
| G5 | rFAdV9-435 | SC (6.1 DP/0.2 mL) | IM (6.5 DP/0.5 mL) | 10 | 10 | 10 |
| G6 | Non-vaccinated control | — | — | 10 | 10 | 10 |

Example 7A. Potency Assessment

All the groups were observed daily during 10 days after each challenge. In order to perform a clinical assessment, each chicken was inspected individually and it was given a numerical value according to the clinical changes observed, according to Table 3.

Figure 17:
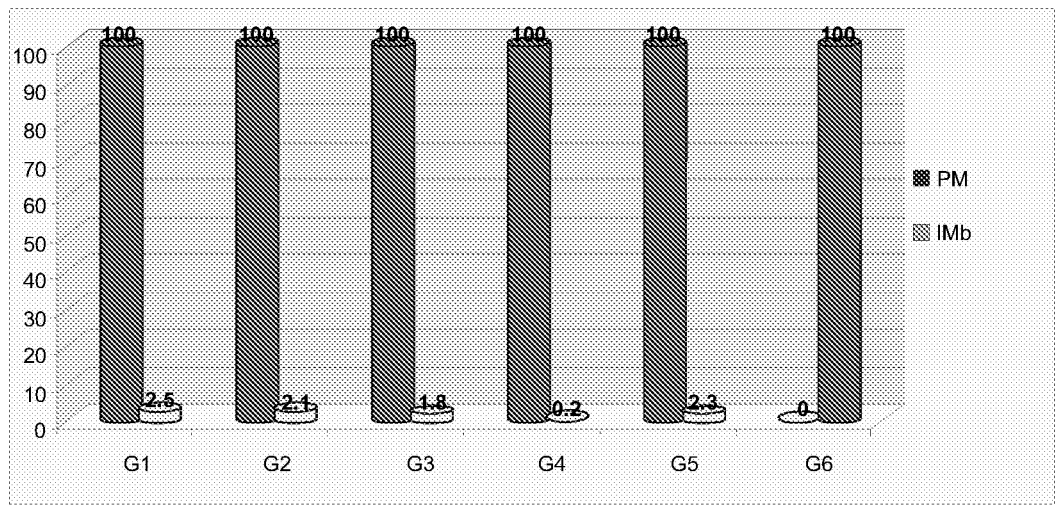
FIG. 17 is a graph showing potency results of CRL chicks immunized at 1 DE, with or without re-vaccination at 10 DE and challenged at 31 DE.
Figure 18:
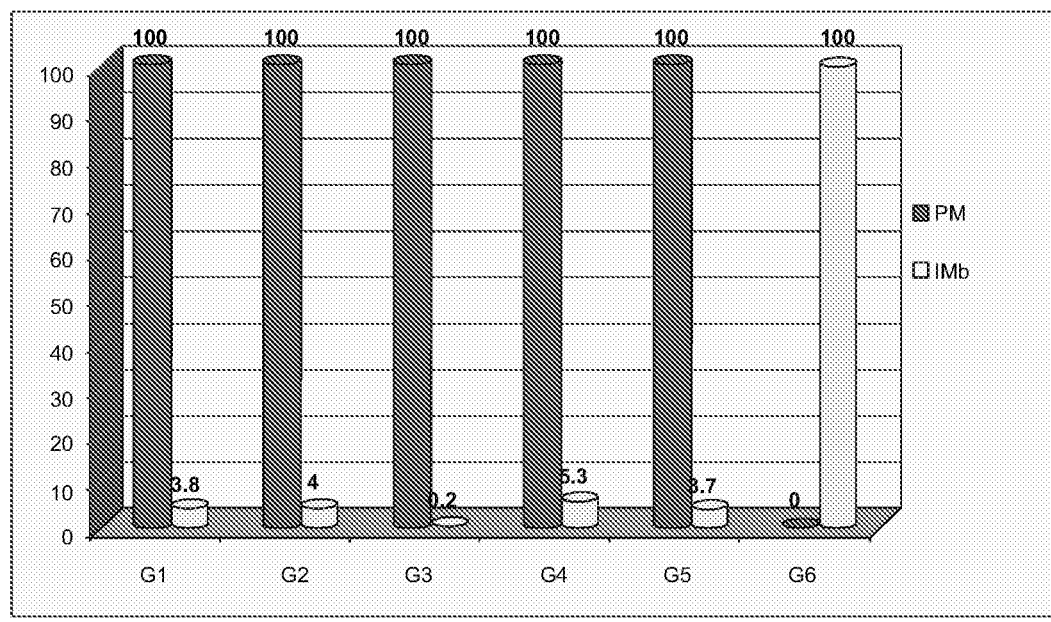
FIG. 18 is a graph showing potency results of CRL chicks immunized at 1 DE, with or without re-vaccination at 10 DE and challenged at 93 DE.

M and IMb were calculated in accordance to what is indicated in Example 6A. The results are shown in FIGS. 16 to 18.

The potency results before an early challenge at 19 DE, indicated that the rFAdV9-435 vectorized vaccine applied via SC at a rate of 0.2 mL with 7.1 DP combined with the HVT vaccine in the Marek vaccine diluent itself or alone, generated protections at a mortality (PM) of 70% with low IMb, of 18.4% and 19.3% respectively. This result confirms that the immunogenic potential of the rFAdV9-435 vaccine is not affected by the HVT vaccine against Marek.

Figure 16:
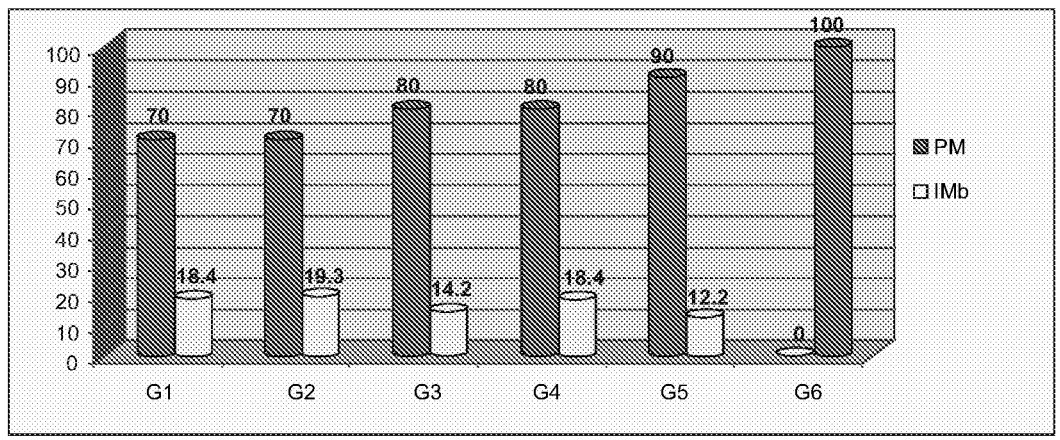
FIG. 16 is a graph showing potency results of CRL chicks immunized at 1 DE, with or without re-vaccination at 10 DE and challenged at 19 DE.

The potency results before an early challenge at 19 DE show that the rFAdV9-435 vectorized vaccine applied along with the Marek HVT vaccine or alone, generates PM between 70% and 90% and low IMb (see FIG. 16). This result confirms that the immunogenic potential of the rFAdV9-435 vaccine is not affected by the HVT vaccine against Marek.

Likewise, these results indicate that only one application of 6.1 DP a day after birth of the rFAdV9-435 vaccine, confers to the birds a protection similar to when a single application of 7.1 DP is administered or that when a second dose is administered at 10 DE.

In the case of the challenge at 31 DE, the results observed in FIG. 17 indicate that the rFAdV9-435 vectorized vaccine applied via SC, alone or in combination with the HVT vaccine against Marek, generated a PM of 100% with practically null IMb in all the immunized groups, with which it is also confirmed that the immunogenic potential of the rFAdV9-435 vaccine is not affected by the HVT vaccine against Marek.

Likewise, it is observed that a single application of 6.1 DP of the rFAdV9-435 vaccine is enough to confer excellent protection to the challenge at 31 DE.

In the same way, in FIG. 18 the potency results before a late challenge at 93 DE indicate that the sectorized vaccine of the present invention, applied alone or in combination with the HVT vaccine against Marek, generated a PM of 100% and practically null IMb. With that, it is shown that the rFAdV9-435 vaccine keeps the same immunogenic potential at least up to 93 DE, even utilizing a single dose of 6.1 DP administered one day after birth.

Example 78. Immunogenicity Assessment

Serum samples were obtained from all the groups at 19, 31 and 03 DE, which were kept at −20° C. until use. Serialized double dilutions of the sera were faced with 4 hemagglutinant units (UHA) of VIABP-435 in an IH test.

Figure 19:
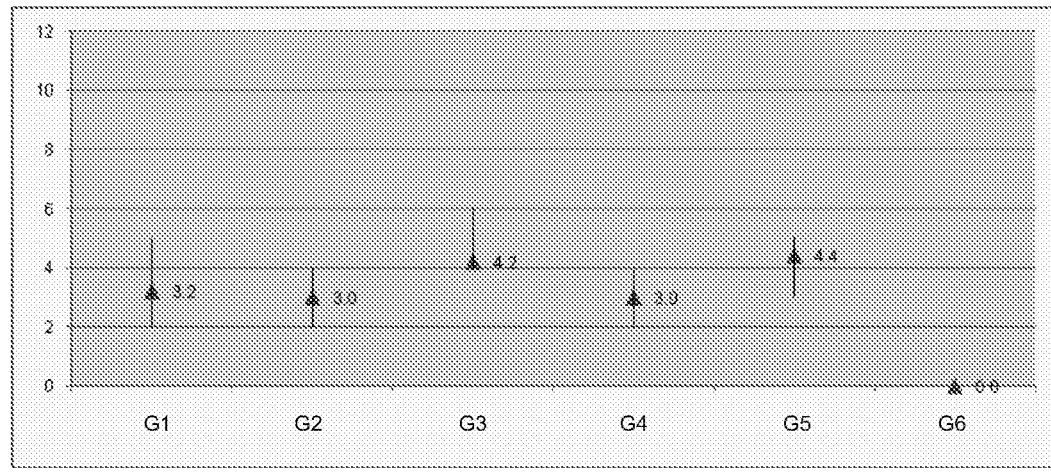
FIG. 19 is a graph showing the IH results of CRL chicks immunized at 1 DE, with or without re-vaccination at 10 DE, with sera taken at 19 DE.
Figure 20:
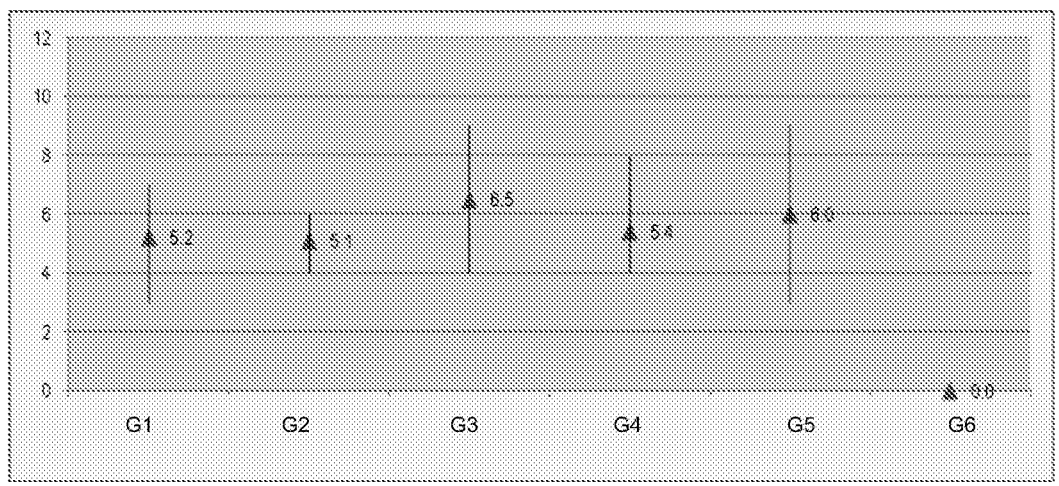
FIG. 20 is a graph showing the IH results of CRL chicks immunized at 1 DE, with or without re-vaccination at 10 DE, with sera taken at 31 DE.
Figure 21:
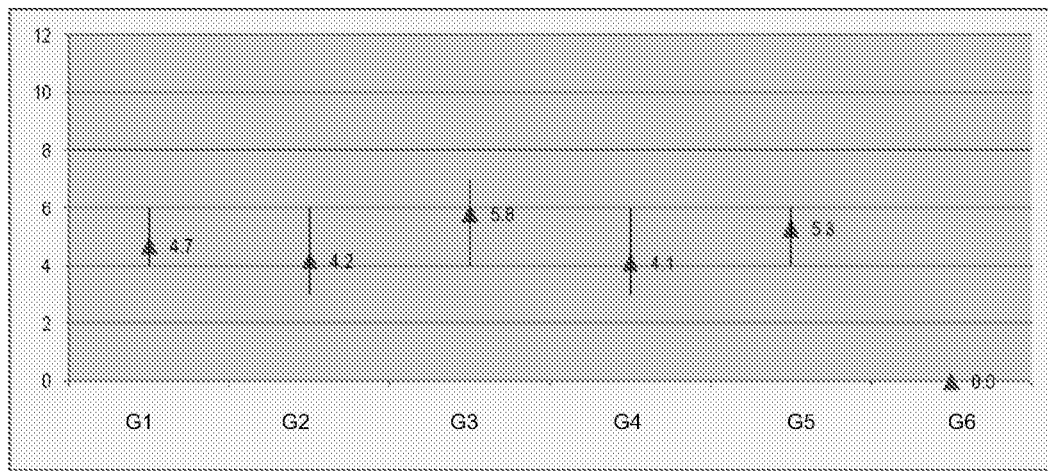
FIG. 21 is a graph showing the IH results of CRL chicks immunized at 1 DE, with or without re-vaccination at 10 DE with sera taken at 93 DE.

The results are summarized in FIGS. 19 to 21, where an analogy can be observed with the results of PM and IMb, since the antibody levels measured in immunized groups for the challenges performed at 19, 31 and 93 DE are similar for all the vaccines tested.

Example 8. Efficacy of rFAdV9-435 Recombinant Active Vaccine Applied Via IM, in Comparison with Application Via SC, and Detection of HVT Virus of Marek's Disease on Feathers Follicle 330 LPE chicks were employed, divided into 22 groups of 15 birds each, in accordance to what is shown in Table 6. Vaccines were administered at 1 DE, as well as at different hours after birth (HE) and DE (except for the non-vaccinated control group), alone or in combination with an HVT commercial vaccine against Marek, which had a titer of 4200 UFP/mL and it was employed according to the commercial laboratory indications.

The birds were housed in isolation units, where they were challenged at 31 DE ocularly and through the nostrils with 0.3 mL of VIAAP-H5N2 (strain A/chicken/Querétaro/14588-19/95), applying a dose of $10^{8.0}$DIEP50% to each chicken.

TABLE 6

Treatment groups with the rFAdV9-435 vaccine and/or HVT.

| Group | 1 DE | 2 HE | 4 DE | 10 DE | 14 DE | Challenges at 31 DE |
|---|---|---|---|---|---|---|
| G1 | SC rFAdV9-435 (7.1 DP) + HVT (mixed) | | | | | 10 |
| G2 | SC rFAdV9-435 (7.1 DP) + SC HVT | | | | | 10 |
| G3 | SC rFAdV9-435 (6.1 DP) + HVT (mixed) | | | | | 10 |
| G4 | SC rFAdV9-435 (6.1 DP) + SC HVT | | | | | 10 |
| G5 | SC HVT | SC rFAdV9-435 (7.1 DP) | | | | 10 |
| G6 | SC HVT | | SC rFAdV9-435 (7.1 DP) | | | 10 |

TABLE 6-continued

Treatment groups with the rFAdV9-435 vaccine and/or HVT.

| Group | 1 DE | 2 HE | 4 DE | 10 DE | 14 DE | Challenges at 31 DE |
|---|---|---|---|---|---|---|
| G7 | SC HVT | | | SC rFAdV9-435 (7.1 DP) | | 10 |
| G8 | SC HVT | | | SC rFAdV9-435 (6.1 DP) | | 10 |
| G9 | SC HVT | | | | SC rFAdV9-435 (7.1 DP) | 10 |
| G10 | SC HVT | | | | | 10 |
| G11 | SC rFAdV9-435 (7.1 DP) | | | | | 10 |
| G12 | SC rFAdV9-435 (6.1) | | | | | 10 |
| G13 | IM rFAdV9-435 (7.1 DP) + SC HVT | | | | | 10 |
| G14 | IM rFAdV9-435 (6.1) + SC HVT | | | | | 10 |
| G15 | SC HVT | IM rFAdV9-435 (7.1 DP) | | | | 10 |
| G16 | SC HVT | | IM rFAdV9-435 (7.1 DP) | | | 10 |
| G17 | SC HVT | | | IM rFAdV9-435 (7.1 DP) | | 10 |
| G18 | SC HVT | | | IM rFAdV9-435 (6.1 DP) | | 10 |
| G19 | SC HVT | | | | IM rFAdV9-435 (7.1 DP) | 10 |
| G20 | IM rFAdV9-435 (7.1) | | | | | 10 |
| G21 | IM rFAdV9-435 (6.1) | | | | | 10 |
| G22 | Non-vaccinated control | | | | | 10 |

Example 8A. Marek's Virus HVT Strain Detection 15 days after vaccination (PV), three feather follicles from five chickens of each of the immunized groups and of the non-vaccinated control group were obtained and used to prepare a macerated mass in a 1:5 ratio with PBS at pH 7.2 and PCR and PCRtr tests were performed on the samples. The tests results are shown in Table 7.

TABLE 7

Results obtained from treatment groups with the rFAdV9-435 and/or HVT vaccine

| Group | PCR/HVT a 15 days PV | PCRtr/HVT a 15 days PV | VIAAP challenge protection at 31 DE | IMb |
|---|---|---|---|---|
| G1 | Pos | $1.6 \times 10^6$ | 100% | 1.2 |
| G2 | Pos | $6.4 \times 10^6$ | 100% | 2.3 |
| G3 | Pos | $3.1 \times 10^6$ | 100% | 0.8 |
| G4 | Pos | $5.5 \times 10^6$ | 100% | 1.2 |
| G5 | Pos | $7.1 \times 10^6$ | 100% | 0.7 |
| G6 | Pos | $7.8 \times 10^6$ | 100% | 2.1 |
| G7 | Pos | $5.9 \times 10^6$ | 100% | 0.0 |
| G8 | Pos | $5.0 \times 10^6$ | 100% | 0.1 |
| G9 | Pos | $8.3 \times 10^6$ | 100% | 2.3 |
| G10 | Pos | $9.7 \times 10^6$ | 0% | 100% |
| G11 | Neg | Neg | 100% | 1.0 |
| G12 | Neg | Neg | 100% | 2.3 |
| G13 | Pos | $2.4 \times 10^6$ | 100% | 1.2 |
| G14 | Pos | $3.4 \times 10^6$ | 100% | 2.6 |
| G15 | Pos | $3.2 \times 10^6$ | 100% | 1.3 |
| G16 | Pos | $5.7 \times 10^6$ | 100% | 2.4. |

TABLE 7-continued

Results obtained from treatment groups with the rFAdV-435 and/or HVT vaccine

| Group | PCR/HVT a 15 days PV | PCRtr/HVT a 15 days PV | VIAAP challenge protection at 31 DE | IMb |
|---|---|---|---|---|
| G17 | Pos | $1.3 \times 10^6$ | 100% | 2.0 |
| G18 | Pos | $2.6 \times 10^6$ | 100% | 1.7 |
| G19 | Pos | $4.9 \times 10^6$ | 100% | 2.0 |
| G20 | Neg | Neg | 100% | 1.8 |
| G21 | Neg | Neg | 100% | 2.6 |
| G22 | Neg | Neg | 0% | 100% |

As can be observed, all the groups vaccinated with the HVT strain vaccine against Marek alone or with rFAdV-435 with the different vaccination calendars, resulted positive to the PCR test specific for HVT virus detection on a feather follicle. In contrast, groups immunized only with rFAdV-435 and the non-vaccinated control resulted negative for the same PCR/HVT test.

Regarding the PCRtr results, the result for the group vaccinated only with the HVT vaccine was of $9.7 \times 10^{6.0}$, whereas for all the vaccinated groups with the different calendars with application of HVT and rFAdV9-435, the results varied from $1.6 \times 10^{6.0}$ up to $8.3 \times 10^{6.0}$. In the case of groups vaccinated exclusively with rFAdV9-435 and the non-vaccinated control group, the results were negative.

According to the route of administration of the rFAdV-435 vaccine (SC or IM) and the HVT virus pathogeny of Marek's disease (SC), the results both for PCR and PCRtr indicate that the HVT vaccine virus could replicate suitably in the different organs and was ultimately housed in feathers follicles, whereby the differences (non-significant) in the base 10 logarithm detected in the PCRtr test are not indicative of the rFAdV9-435 vaccine interfering with the HVT virus replication, or its viral load or circulation in an organism to such a degree that a suitable HVT vaccine immune response is avoided.

Example 88. Potency Assessment

All the groups were observed daily during 10 days after the challenge (PD). In order to perform a clinical assessment, each chicken was inspected individually and it was given a numerical value according to the clinical changes observed, according to Table 3.

PM and IMb were calculated in accordance to what is indicated in Example 6A. The results are also shown in Table 7.

The potency results indicate that the rFAdV9-435 vaccine applied via SC or IM, with or without the HVT vaccine and with the different vaccination calendars, was able to generate an excellent 100% PM and a practically null IMb for all the cases, in contrast with the non-vaccinated control for which the PM was 0% with a maximum IMb of 100%.

On the basis of the results from examples 8A and 8B, it can be said that the HVT strain vaccine against Marek's disease and the rFAdV9-435 vaccine against IAAP-H5N2, can be employed jointly without affecting the immune response of neither of the two vaccines.

Example 9. Efficacy of rFAdV9-435 Recombinant Active Vaccine Applied Via IM, in Comparison to Application Via SC 5 groups of 10 LPE chickens each were formed, 4 of which were vaccinated and 1 was left as a non-vaccinated control, according to Table 8.

The chickens were housed in isolation units and challenged at 31 DE ocularly and through the nostrils with 0.3 mL of VIAAP-H5N2 (strain A/chicken/Querétaro/14588-19/95), applying 7.5 DP to each chicken.

TABLE 8

Treatment groups with the rFAdV9-435 vaccine.

| | | Application days, doses and vaccines administration route | | | Challenges with VIAAP-H5N2 |
|---|---|---|---|---|---|
| Group | Vaccines | 1 DE | 10 DE | | 31 DE |
| G1 | rFAdV9-435 | IM (6.1 DP/0.2 mL) | | | 10 |
| G2 | rFAdV9-435 | | IM (6.5 DP/0.5 mL) | | 10 |
| G3 | rFAdV9-435 | SC (6.1 DP/0.2 mL) | | | 10 |
| G4 | rFAdV9-435 | | SC (6.5 DP/0.5 mL) | | 10 |
| G5 | Not vaccinated control | — | — | | 10 |

Example 9A. Potency Assessment

All the groups were observed daily during 10 days PD. In order to perform a clinical assessment, each chicken was inspected individually and it was given a numerical value according to the clinical changes observed, according to Table 3.

Figure 22:
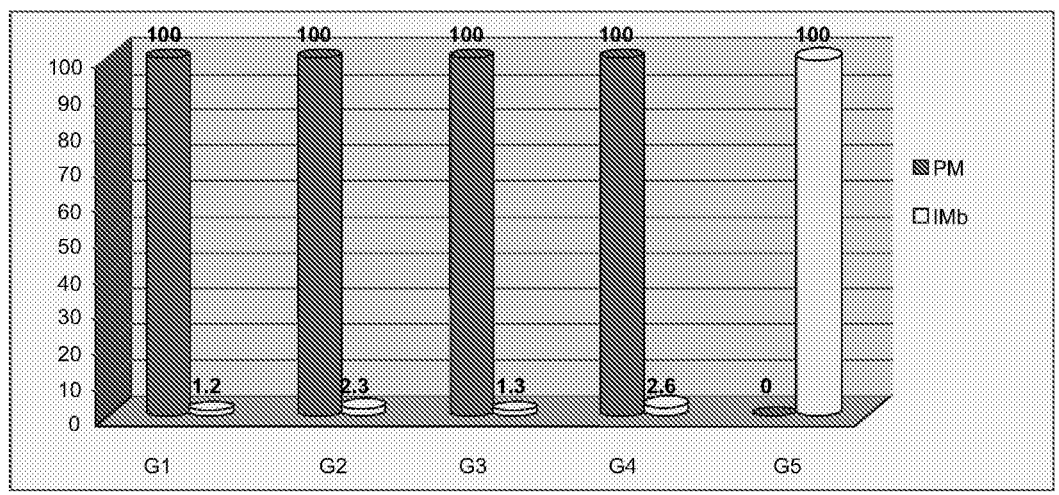
FIG. 22 is a graph showing potency results of chicks Free of Specific Pathogens (LPE) immunized at 1 and 10 DE, and challenged at 31 DE.

PM and IMb were calculated in accordance to what is indicated in Example 6A. The results are shown in FIG. 22.

The potency results before the challenge at 31 DE with VIAAP-H5N2, indicate that the rFAdV9-435 vectorized vaccine applied via IM a day after birth at G1 and G2 conferred a PM of 100% with IMb of 1.2 and 2.3 respectively. The results from G3 and G4, immunized via SC were 100% PM and IMb of 1.3 and 2.6, which confirms usage viability of the SC route, as well as the IM route, for the administration of the rFAdV9-435 vaccine.

Example 98. Immunogenicity Assessment

Serum samples were obtained from all the groups at 31 DE, which were kept at −20° C. until use. Serialized double dilutions of the sera were faced with 4 hemagglutinant units (UHA) of VIABP-435 in an IH test.

Figure 23:
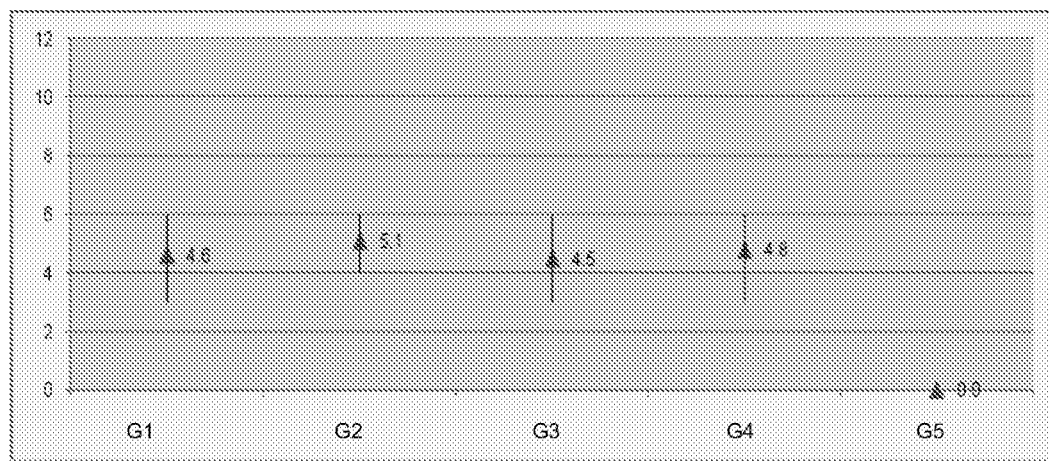
FIG. 23 is a graph showing IH results of LPE chicks immunized at 1 and 10 DE, with sera taken at 31 DE.

The IH tests results are shown in FIG. 23. Sera taken at 31 DE reflect a mean of $2^{4.8}$, $2^{5.1}$, $2^{4.5}$ and $2^{4.8}$ for G1, G2, G3 and G4 respectively, indicating high correlation with the protection of birds before the challenge.

These results confirm that the vaccine of the present invention is equally effective at inducing circulating antibodies when administered via IM and when administered via SC.

Example 10. In Vivo Assessment of rFAdV9-gB Recombinant Active Vaccine Against Avian Infectious Laryngotracheitis In a similar way to what is described in Example 5, a recombinant vaccine in avian adenovirus vector with glycoprotein B insert of avian infectious laryngotracheitis (LTI), called rFAdV9-gB vaccine was made and its effectiveness was tested.

90 LPE chickens, divided into 9 groups of 10 birds each, 1 non-vaccinated control group, 1 non-vaccinated control and non-challenged group and 7 groups immunized with the following vaccines were employed: a) rFAdV9-gB vaccine; and b) commercial vaccine with chicken embryo modified active virus (CEP-LTI). The groups were immunized in accordance to what is shown in Table 9.

The animals were housed in isolation units and challenged at 31 DE with high viral load LTI virus (vvLTI), USA 63,140 strain, which was applied to each chicken at a dose rate of 3.9 DP in 0.3 mL, applying two drops on each eye and 3 drops on each nostril.

TABLE 9

Treatment groups with the FAdV9-gB vaccine

| Group | Doses and application of vaccines against LTI, via SC and ocularly (O) at 1, 4 and 10 DE | | | Challenge with vvLTI |
|---|---|---|---|---|
| | 1 DE | 4 DE | 10 DE | 31 DE |
| G1 | SC rFAdV9-gB (7.1 DP/0.2 mL) | | | 10 |
| G2 | | | SC rFAdV9-gB (7.5 DP/0.5 mL) | 10 |
| G3 | SC rFAdV9-gB (7.1 DP/0.2 mL) | | SC rFAdV9-gB (7.5 DP/0.5 mL) | 10 |
| G4 | SC rFAdV9-gB (6.1 DP/0.2 mL) | | | 10 |
| G5 | | | SC rFAdV9-gB (6.5 DP/0.5 mL) | 10 |
| G6 | SC rFAdV9-gB (6.1 DP/0.2 mL) | | SC rFAdV9-gB (6.5 DP/0.5 mL) | 10 |
| G7 | | | O CEP-LTI (3.1 DP/0.03 MI) | 10 |
| G8 | Non-vaccinated control | | | 10 |
| G9 | Neither vaccinated nor challenged | | | 10 |

Example 10A. Potency Assessment

All the groups were observed daily during 9 days PD. In order to perform a clinical assessment, each chicken was inspected individually and it was given a numerical value according to the clinical changes observed, according to Table 3.

M and IMb were calculated in accordance to what is indicated in Example 6A. The results are shown in Table 10.

The IMb results observed in the different groups of vaccinated LPI chickens indicated that 9 days PD, with vvLTI, clinical signs were generally of a low to moderate intensity, lower than those observed for G8, non-vaccinated control.

For G1, G2 and G3, immunized with 7.1 and/or 7.5 DP of the rFAd9-gB vaccine via SC, the IMb were 6.2, 6.1 and 3.5 respectively, whereas for groups G4, G5 and G6, immunized with a 10 times lower dose of the rFAdV9-gB vaccine (6.1 and/or 6.5 DP), similar IMb were obtained, of 6.5, 6.3 and 5.2, respectively (Table 10). These results indicate that the use of a 10 times lower dose of rFAdV9-gB vectorized vaccine did not represent a significant difference in order to protect vaccinated birds against the appearance of clinical signs of LT in immunized birds. On the other hand, they show that the recombinant vaccine of the present invention, with a gen gB insert of the LTI virus, rFAdV9-gB, showed a result to prevent lesions on the larynx and trachea slightly inferior to the CEP-LTI commercial vaccine.

Regarding M, it was not observed in either group.

TABLE 10 rFAdV-gB vaccine efficacy

| Group | IMb | Macroscopic lesions degree of the group |
|---|---|---|
| G1 | 6.2 | ++ |
| G2 | 6.1 | ++ |
| G3 | 3.5 | ++ |
| G4 | 6.5 | ++ |
| G5 | 6.3 | ++ |
| G6 | 5.2 | ++ |
| G7 | 2.4 | + |
| G8 | 37.0 | +++++ |
| G9 | 0 | − |

Example 10B. Potency Assessment on Macroscopic Lesions Prevention

Nine days after the challenges the birds from all groups were sacrificed, larynges and tracheas from birds in each group were inspected to determine whether there were macroscopic lesions (presence of serous exudate and petequial hemorrhages on the larynx and trachea submucose), comparing the degree of macroscopic changes with the non-vaccinated but challenged G8 to which number five (+++++) was assigned, and the neither vaccinated nor challenged control group (called G9) to which number zero (−) was assigned.

The macroscopic lesions prevention results observed in the different groups of vaccinated LPE chickens, also shown in Table 10, indicate that all groups immunized with the rFAdV9-gB vaccine, (even for G4, G5 and G6, to which a 10 times lower dose of this vaccine was applied), showed similar macroscopic lesions protection indexes, very close to the protection generated by the CEP-LTI commercial vaccine.

These results confirm that the use of a 10 times lower dose of rFAdV9-gB did not represent a significant difference in reducing the appearance of macroscopic lesions on immunized birds, and that with it it is possible to obtain results close to those obtained with a commercial vaccines made with a complete virus and propagated in a chicken embryo, without taking the risks it entails.

According to the above-described, it may be seen that the recombinant vaccine in serotype-9 fowl adenovirus vector, has been devised to have an stable recombinant vaccine, resulting effective even when administered in combination with a Marek's disease vaccine, and which efficacy is non-affected by the presence of maternal antibodies, and it will be apparent for any skilled in the art that the embodiments of the recombinant vaccine in serotype-9 fowl adenovirus vector and the use thereof, according to the above-described and illustrated in the enclosed drawings, are only illustrative and non-limiting of the present invention, since several changes of consideration in its details are possible without departing from the scope of the invention. For example, it has been experimentally shown that it is possible to achieve stability in successive passes of cell cultures with diverse exogenous genes and that it is possible to utilize different types of acceptable vehicles for vaccine formulation.

Therefore, the present invention should not be considered restricted except by the prior art demands and by the scope of the appended claims.

What is claimed is:

1. A recombinant vaccine comprising a serotype 9 fowl adenovirus vector (FAdV-9) having at least one exogenous nucleotide sequence inserted encoding at least one antigen of a disease of interest and replacing the adenovirus genome non-essential region, and a pharmaceutically acceptable vehicle, adjuvant and/or excipient, wherein the FAdV-9 vector is live, and the exogenous nucleotide sequence is located between the 491 and 2782 nucleotides, and wherein the recombinant vaccine provides protection, with one dose, up to at least 90 days after its administration.

2. The recombinant vaccine according to claim 1, wherein the FAdV-9 vector comprises the sequence SEQ ID NO: 1.

3. The recombinant vaccine according to claim 1, wherein the exogenous nucleotide sequence encodes at least one antigen of a disease of interest, selected from avian influenza, birds infectious laryngotracheitis, Newcastle's disease, bursa of Fabricius infection, infectious bronchitis, disease caused by metapneumovirus (MPNV), Marek's disease, birds infectious anemia and any other gene which size allows insertion in the FAdV-9 vector.

4. The recombinant vaccine according to claim 3, wherein the exogenous nucleotide sequence encodes an antigen of the group comprising hemagglutinin (HA) of the avian influenza virus; glycoprotein B (gB) and glycoprotein D (gD) infectious laryngotracheitis virus from birds (LTI); HN and F proteins of the virus of Newcastle's disease; VP2 protein virus infection of the bursa of Fabricius; S1 and S2 protein of the infectious bronchitis virus; F protein of metapneumovirus (MPNV); and VP1, VP2 and VP3 protein of infectious anemia in birds.

5. The recombinant vaccine according to claim 4, wherein the HA of the avian influenza virus is selected from at least one of the H1, H2, H3, H5, H6, H7 or H9 subtypes of said protein.

6. The recombinant vaccine according to claim 1, wherein the exogenous nucleotide sequence comprises a gene encoding at least one antigen of a fowl adenovirus different from the FAdV-9 utilized as viral vector.

7. The recombinant vaccine according to claim 1, wherein the virus concentration is at least of 105.0 DICC 50% per dose.

8. The recombinant vaccine according to claim 7, wherein the virus concentration is at least of 106.0 DICC 50% per dose.

9. The recombinant vaccine according to claim 1, wherein the pharmaceutically acceptable vehicles are aqueous solutions, selected from the group consisting of aqueous solutions comprising trehalose, phosphate, glutamate, albumin (TPGA) stabilizer; aqueous solutions comprising peptone stabilizer; and aqueous solutions comprising skimmed milk.

10. The recombinant vaccine according to claim 1, wherein the vaccine is prepared to be administered intramuscularly, intranasally, subcutaneously, by spraying, nebulization, orally or through drinking water, or in ovo.

11. The recombinant vaccine according to claim 1, comprising a Marek's disease whole virus vaccine.

12. The recombinant vaccine according to claim 1, comprising an FAdV-9 vector having at least two exogenous nucleotide sequences inserted encoding at least two antigens either from the same disease of interest or different diseases of interest, and replacing the genome non-essential region of the adenovirus, located between the 491 and 2782 nucleotides.

13. The recombinant vaccine according to claim 1, comprising at least a second vaccine based on an FAdV-9 vector having at least one exogenous nucleotide sequence inserted encoding at least one antigen different from that of the first vaccine, either of the same disease of interest or a different one, and replacing the genome non-essential region of the adenovirus, located between the 491 and 2782 nucleotides.

14. A master seed of a serotype-9 fowl adenovirus recombinant virus (FAdV-9) which has an exogenous nucleotide sequence inserted encoding a disease of interest antigen and replacing the adenovirus genome non-essential region, located between the 491 and 2782 nucleotides, wherein it is obtained after 6 to 11 passes in cell culture.

15. A method of generating an immune response in an animal by administering an effective amount of the recombinant vaccine of claim 1 to an animal in need thereof.

16. The method according to claim 15, wherein administering comprises two or more doses.

17. The method according to claim 15, wherein administering comprises a single dose.

18. The method according to claim 17, wherein the recombinant vaccine is administered alone or jointly with other recombinant or non-recombinant, live or inactivated vaccines.

19. The method according to claim 15, wherein the recombinant vaccine is administered jointly with a vaccine against Marek's disease.

20. The method according to claim 15, wherein administration of one dose of the recombinant vaccine provides protection up to at least 90 days.

* * * * *

SEQUENCE LISTING

<160> NUMBER OF SEQ ID NOS: 2

<210> SEQ ID NO 1
<211> LENGTH: 593
<212> TYPE: DNA
<213> ORGANISM: Fowl adenovirus 9

<400> SEQUENCE: 1

```
atgggagcca cctacttcga catcaagggc gttctagaca gaggaccttc ttttaaacca      60
tacggaggaa ccgcatacaa tcccctcgcg ccccgcgaag ccttttcaa caattggctt     120
gagtcagagc cgaacaagac cgtcattacg gggttaatga ccacccccta ccgaaacgac     180
caggggaaca agaccaatac tgctgacgta gttaatagcg tgtcgggagt ttatccgaac     240
cccaatctcg gaccctgcat cagcgagatg ggagcactgg atgatgcaac tgctgacctt     300
gtcggctttg cgggacggtt tgcgaaagtt acaaacgaga atacgcgttt ggcatacgga     360
gcgtatgtga aaccgttgaa aaacgatggt tcgcagtcat taaacccac tccttactgg      420
gtaatggaca agactgacgc caagtatctg ggcgtgatgg ccgtggaaga tttcagcacc     480
agtctcacct atccggacag cttgttaatc cctccgccct cggactactc aaccgttaac     540
acgggcgcaa tgaaagcaaa ccgtcctaac tacatcggtt tcagagataa ctt           593
```

<210> SEQ ID NO 2
<211> LENGTH: 1695
<212> TYPE: DNA
<213> ORGANISM: Influenza A virus

<400> SEQUENCE: 2

```
atggaaagaa tagtgattgc ctttgcaata atcagcattg ttacaggtga ccaaatctgc      60
attggttatc atgcaaacaa ttcaacaaaa caagttgata caatcatgga aaagaatgtg     120
acggtcacac atgctcagga catactagaa aaagaacaca atggaagact ctgcagtctt     180
aaaggagtaa agcccctcat cctgaaggat tgcagcgtag ctgggtggat tctgggaaat     240
cctatgtgtg gtgaattcct gaatgtgccg gaatggtcat acattgtgga gaagacaac     300
ccatccaatg gcctgtgtta ccctggaaac ttcgacaatt atgaagaatt gaagcattta    360
atgagcagca caaatcacat cgagagaatt cagatatttc taggagctc ttggtccaac    420
cataatgcct catcaggagt gagctcggca tgcccgtcca atgtatatc ttcctttttc    480
cggaatgtag tgtggttgat caagaaggat aatgtgtacc gaacactaaa gaagaactac    540
accaacacca atgtagaaga cctttaata atgtggggag ttcatcaccc tactgatgca    600
actgagcaga caaaactcta ccagaacctg aacacttatg tatcggtggg aacatcaaca    660
ctaaatcaga ggtcaatccc gaaaatagcc accagacccc aggtgaacgg acagagagga    720
aggatggaat ttttttggac aatattaaag ccgaacgatt caatctttt tgagagtact    780
gggaacttta tagctcccga atatgcatac aagatcacta aaaagggaa atcagcagtc    840
atgaaaagtg aactggatta tggcgactgt aataccaaat gccagacccc agtgggtgct    900
```

```
gtaaattcca gtctgccttt ccacaatgtc catcccttta ccattgggga atgccccagg    960
tatgtaaaat cgaagaaact ggtccttgca acaggattaa gaaatgtacc ccaaaaagaa   1020
acaagaggct tatttggagc aatagctgga ttcatagaag gggggtggca aggaatggtg   1080
gatggatggt atggatacca tcatagcaat gagcagggta gtgggtatgc tgcagacaaa   1140
gaatctacac agaaagcaat taatggaatc actaataaag tcaactcaat cattggcaaa   1200
atgaacactc agttcgaagc cattgggaaa gaattcaaca acctagaaag gagaatagaa   1260
aatttgaata agaaaatgga agatgacttt ttggatgtat ggacttacaa tgcagaactt   1320
ctagtgctca tggaaaacga gagaactctg gatctccatg attcaaatgt caagaattta   1380
tacgataagg tccgactcca actgagagat aatgcaaaag aactaggcaa cggatgcttt   1440
gaattctacc acaagtgtga caatgaatgc atggaaagtg tgagaaatgg aacgtatgat   1500
tacccacaat actcaaaaga gtcaaaactg aatagagagg aaatagaagg ggtcaaatta   1560
gaatcaacag ggacttatca gatactttca atctattcaa cagtggcgag ttccctagca   1620
ctggcaatca tggtagctgg tctatctttt tggatgtgct ccaatggatc attgcagtgc   1680
agaatttgca tctaa                                                    1695
```